US011819533B2

(12) United States Patent
Bartizal et al.

(10) Patent No.: US 11,819,533 B2
(45) Date of Patent: *Nov. 21, 2023

(54) COMPOSITIONS AND METHODS FOR THE TREATMENT OF FUNGAL INFECTIONS

(71) Applicant: Cidara Therapeutics, Inc., San Diego, CA (US)

(72) Inventors: Kenneth Bartizal, La Jolla, CA (US); Paul Daruwala, Del Mar, CA (US); David Hughes, San Diego, CA (US); Martin Patrick Hughes, Spokane, WA (US); Navdeep B. Malkar, Cary, NC (US); Balasingam Radhakrishnan, Chapel Hill, NC (US); Anuradha Vaidya, Cary, NC (US)

(73) Assignee: Cidara Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/539,727

(22) Filed: Dec. 1, 2021

(65) Prior Publication Data

US 2022/0323539 A1 Oct. 13, 2022

Related U.S. Application Data

(63) Continuation of application No. 16/629,711, filed as application No. PCT/US2018/041617 on Jul. 11, 2018, now Pat. No. 11,197,909.

(60) Provisional application No. 62/531,788, filed on Jul. 12, 2017.

(51) Int. Cl.
*A61K 38/12* (2006.01)
*A61P 31/10* (2006.01)
*A61K 47/26* (2006.01)
*A61K 9/00* (2006.01)

(52) U.S. Cl.
CPC .............. *A61K 38/12* (2013.01); *A61K 47/26* (2013.01); *A61P 31/10* (2018.01); *A61K 9/0019* (2013.01)

(58) Field of Classification Search
CPC .......... A61K 38/08; A61K 38/12; C07K 7/04; C07K 7/56
See application file for complete search history.

(56) References Cited

U.S. PATENT DOCUMENTS

| | | |
|---|---|---|
| 4,427,660 A | 1/1984 | Schiffman et al. |
| 5,166,135 A | 11/1992 | Schmatz |
| 5,378,804 A | 1/1995 | Balkovec et al. |
| 5,399,552 A | 3/1995 | Bouffard |
| 5,514,651 A | 5/1996 | Balkovec et al. |
| 5,516,756 A | 5/1996 | Balkovec et al. |
| 5,541,160 A | 7/1996 | Balkovec et al. |
| 5,652,213 A | 7/1997 | Jamison et al. |
| 5,741,775 A | 4/1998 | Balkovec et al. |
| 5,854,213 A | 12/1998 | Bouffard |
| 5,948,753 A | 9/1999 | Balkovec et al. |
| 6,030,944 A | 2/2000 | Bouffard et al. |
| 6,069,126 A | 5/2000 | Abruzzo et al. |
| 6,268,338 B1 | 7/2001 | Balkovec et al. |
| 6,506,726 B1 | 1/2003 | Dobbins et al. |
| 6,821,951 B2 | 11/2004 | Schwier et al. |
| 7,198,796 B2 | 4/2007 | Stogniew |
| 7,452,861 B2 | 11/2008 | Kaniga |
| 8,722,619 B2 | 5/2014 | James, Jr. et al. |
| 9,217,014 B2 | 12/2015 | James, Jr. et al. |
| 9,526,835 B2 | 12/2016 | Radhakrishnan et al. |
| 9,676,821 B2 | 6/2017 | James, Jr. et al. |
| 10,016,479 B2 | 7/2018 | Radhakrishnan et al. |
| 10,369,188 B2 | 8/2019 | Bartizal et al. |
| 10,702,573 B2 | 7/2020 | Radhakrishnan et al. |
| 10,780,144 B2 | 9/2020 | Bartizal et al. |
| 11,197,909 B2 | 12/2021 | Bartizal et al. |
| 11,524,980 B2 | 12/2022 | Hughes et al. |
| 2004/0180965 A1 | 9/2004 | Borgman et al. |
| 2005/0026819 A1 | 2/2005 | Kaniga |
| 2005/0043222 A1 | 2/2005 | Lukacs et al. |
| 2005/0192213 A1 | 9/2005 | Milton et al. |
| 2005/0261173 A1 | 11/2005 | Stogniew |
| 2006/0276339 A1 | 12/2006 | Windsor et al. |
| 2007/0231258 A1 | 10/2007 | Perakyla et al. |
| 2009/0074859 A1 | 3/2009 | Patel |
| 2009/0238867 A1 | 9/2009 | Jenkins et al. |
| 2010/0009009 A1 | 1/2010 | Young et al. |
| 2010/0075302 A1 | 3/2010 | Perlin et al. |
| 2013/0011452 A1 | 1/2013 | Loupenok |

(Continued)

FOREIGN PATENT DOCUMENTS

| | | |
|---|---|---|
| CN | 1222082 A | 7/1999 |
| CN | 1339959 A | 3/2002 |

(Continued)

OTHER PUBLICATIONS

Kuhn et al. Antifungal Susceptibility of Candida Biofilms: Unique Efficacy of Amphotericin B Lipid Formulations and Echinocandins. Antimicrobial Agents And Chemotherapy. Jun. 2002, vol. 46, No. 6, pp. 1773-1780. (Year: 2002).*
U.S. Appl. No. 17/023,884, Bartizal et al., filed Sep. 17, 2020.
U.S. Appl. No. 17/029,784, Balkovec et al., filed Sep. 23, 2020.
U.S. Appl. No. 17/107,627, James et al., filed Nov. 30, 2020.
"Echinocandin Dosing: An Opportunity for Improvement," Institute for Clinical Pharmacodynamics Presentation (2017) (82 pages).

(Continued)

*Primary Examiner* — Jeffrey E. Russel
(74) *Attorney, Agent, or Firm* — Clark & Elbing LLP

(57) ABSTRACT

The disclosure features non-irritating pharmaceutical compositions containing CD101 in pharmaceutical acceptable salt (e.g., CD101 acetate) or neutral form. The pharmaceutical compositions can be intravenously administered to a subject to treat fungal infections (e.g., candidiasis) in the subject.

13 Claims, 10 Drawing Sheets

(56) References Cited

U.S. PATENT DOCUMENTS

| | | |
|---|---|---|
| 2013/0150451 A1 | 6/2013 | Salamone et al. |
| 2013/0197455 A1* | 8/2013 | Zhang ............... A61L 29/16 427/2.3 |
| 2013/0244930 A1 | 9/2013 | James, Jr. et al. |
| 2015/0024997 A1 | 1/2015 | James, Jr. et al. |
| 2015/0087583 A1 | 3/2015 | Radhakrishnan et al. |
| 2016/0045611 A1 | 2/2016 | Hecht et al. |
| 2016/0058717 A1 | 3/2016 | Page et al. |
| 2016/0075740 A1 | 3/2016 | James, Jr. et al. |
| 2016/0213742 A1 | 7/2016 | Forrest et al. |
| 2017/0151306 A1 | 6/2017 | Radhakrishnan et al. |
| 2017/0253635 A1 | 9/2017 | James, Jr. et al. |
| 2018/0256673 A1 | 9/2018 | Balkovec et al. |
| 2019/0000917 A1 | 1/2019 | Bartizal et al. |
| 2019/0160141 A1 | 5/2019 | Radhakrishnan et al. |
| 2019/0216885 A1 | 7/2019 | Bartizal et al. |
| 2019/0307843 A1 | 10/2019 | Bartizal et al. |
| 2019/0374601 A1 | 12/2019 | Bartizal et al. |
| 2020/0268833 A1 | 8/2020 | Bartizal et al. |
| 2021/0002346 A1 | 1/2021 | Bartizal et al. |
| 2021/0128670 A1 | 5/2021 | Radhakrishnan et al. |
| 2022/0162263 A1 | 5/2022 | James, Jr. et al. |

FOREIGN PATENT DOCUMENTS

| | | |
|---|---|---|
| CN | 1355699 A | 6/2002 |
| CN | 101374502 A | 2/2009 |
| CN | 102766198 A | 11/2012 |
| CN | 103889221 A | 6/2014 |
| CN | 104507309 A | 4/2015 |
| CN | 106279369 A | 1/2017 |
| JP | 2006-528188 A | 12/2006 |
| JP | 2014-516339 A | 7/2014 |
| JP | 2015-512392 A | 4/2015 |
| WO | WO-95/08341 A1 | 3/1995 |
| WO | WO-96/08507 A1 | 3/1996 |
| WO | WO-2005/018743 A1 | 3/2005 |
| WO | WO-2008/093060 A2 | 8/2008 |
| WO | WO-2010/032011 A2 | 3/2010 |
| WO | WO-2010/128096 A1 | 11/2010 |
| WO | WO-2011/025785 A1 | 3/2011 |
| WO | WO-2011/025875 A1 | 3/2011 |
| WO | WO-2011/089214 A1 | 7/2011 |
| WO | WO-2012/119065 A2 | 9/2012 |
| WO | WO-2013/017691 A1 | 2/2013 |
| WO | WO-2013/142279 A1 | 9/2013 |
| WO | WO-2014/113693 A1 | 7/2014 |
| WO | WO-2014/124504 A1 | 8/2014 |
| WO | WO-2015/035102 A2 | 3/2015 |
| WO | WO-2017/049102 A1 | 3/2017 |
| WO | WO-2017/049105 A1 | 3/2017 |
| WO | WO-2017/120471 A1 | 7/2017 |
| WO | WO-2017/161016 A1 | 9/2017 |
| WO | WO-2018/085200 A1 | 5/2018 |
| WO | WO-2018/102407 A1 | 6/2018 |
| WO | WO-2018/144600 A1 | 8/2018 |
| WO | WO-2018/187574 A1 | 10/2018 |
| WO | WO-2018/191692 A1 | 10/2018 |
| WO | WO-2019/014333 A1 | 1/2019 |
| WO | WO-2019/027498 A1 | 2/2019 |
| WO | WO-2019/241626 A1 | 12/2019 |

OTHER PUBLICATIONS

"New Hope for Serious Infections," Cidara Therapeutics Corporate Presentation (2017) (39 pages).

Bader et al., "Overcoming the Resistance Hurdle: Pharmacokinetic-Pharmacodynamic Target Attainment Analyses for Rezafungin (CD101) against Candida albicans and Candida glabrata," Antimicrob Agents Chemother. 62(6):e02614-17 (2018) (9 pages).

Barrett, "From natural products to clinically useful antifungals," Biochim Biophys Acta. 1587(2-3):224-33 (2002).

Bastin et al., "Salt selection and optimisation procedures for pharmaceutical new chemical entities," Org. Process Res. Dev. 4(5):427-35 (2000).

Boikov et al., "In vitro activity of the novel echinocandin CD101 at pH 7 and 4 against Candida spp. isolates from patients with vulvovaginal candidiasis," J Antimicrob Chemother. 72(5):1355-8 (2017).

Bouffard et al., "Synthesis and antifungal activity of novel cationic pneumocandin Bo derivatives," J Med Chem. 37(2): 222-5 (1994).

Chandra et al., "Evaluate the Ability of CD101 to Prevent and Treat Candida albicans Biofilms and Explore its Temporal Effect by Time Lapse Photography," 8th Trends in Medical Mycology, Oct. 6-9, Belgrade, Serbia. Abstract Poster No. P057 (2017).

Chatterjee et al., "Draft genome of a commonly misdiagnosed multidrug resistant pathogen Candida auris," BMC Genomics. 16:686 (2015) (16 pages).

Chowdhary et al., "Multidrug-resistant Candida auris: 'new kid on the block' in hospital-associated infections?" J Hosp Infect. 94(3):209-212 (2016).

Communication pursuant to Article 94(3) EPC for European Patent Application No. 13764974.5, dated Nov. 18, 2016 (4 pages).

Crandon et al., "Bronchopulmonary disposition of intravenous voriconazole and anidulafungin given in combination to healthy adults," Antimicrob Agents Chemother. 53(12):5102-7 (2009).

Cuenca-Estrella et al., "Susceptibility of fluconazole-resistant clinical isolates of Candida spp. to echinocandin LY303366, itraconazole and amphotericin B," J Antimicrob Chemother. 46(3): 475-7 (2000).

Cushion et al., "Echinocandin treatment of Pneumocystis pneumonia in rodent models depletes cysts leaving trophic burdens that cannot transmit the infection," PLOS One. 5(1):e8524 (2010) (12 pages).

Cushion et al., "Efficacy of CD101, a novel Echinocandin, in prevention of Pneumocystis Pneumonia (PCP): thwarting the biphasic life cycle of Pneumocystis," Annual Meeting of the American Society of Hematology, Dec. 3-6, San Diego, California, Abstract 3396. Blood. 128(22) (2016) (1 page).

Cushion et al., "Novel Once-Weekly Echinocandin Rezafungin (CD101) for Prevention and Treatment of Pneumocystis Biofilms," European Society for Blood and Marrow Transplantation (EBMT) Annual Meeting, Mar. 18-21, Lisbon, Portugal, Poster, (2018) (1 page).

Cushion, "Prevention of Pneumocystis Pneumonia (PCP) by the novel Echinocandin, CD101," American Society for Microbiology Microbe 2016, Jun. 17, 2016 (17 pages).

Denning et al., "Infectious Disease. How to bolster the antifungal pipeline," Science. 347(6229):1414-6 (2015) (4 pages).

Denning, "Echinocandin antifungal drugs," Lancet. 362(9390):1142-51 (2003).

Douglas et al., "Identification of the FKS1 gene of Candida albicans as the essential target of 1,3-beta-D-glucan synthase inhibitors," Antimicrob Agents Chemother. 41(11):2471-9 (1997).

English translation of Office Action for Japanese Patent Application No. 2013-556894, dated Apr. 21, 2015 (2 pages).

English translation of Search Report for Chinese Application No. 201280021321.9, dated Jan. 6, 2015 (7 pages).

Espinel-Ingroff, "Comparison of in vitro activities of the new triazole SCH56592 and the echinocandins MK-0991 (L-743,872) and LY303366 against opportunistic filamentous and dimorphic fungi and yeasts," J Clin Microbiol. 36(10): 2950-6 (1998).

Extended European Search Report for European Application No. 13764974.5, dated Oct. 26, 2015 (7 pages).

Extended European Search Report for European Patent Application No. 17867743.1, dated Jun. 25, 2020 (12 pages).

Extended European Search Report for International Patent Application No. 12751994.0, dated Jul. 27, 2015 (8 pages).

Fujie et al., "FR131535, a novel water-soluble echinocandin-like lipopeptide: synthesis and biological properties," Bioorg Med Chem Lett. 11(3):399-402 (2001).

Garcia-Effron et al., "Effect of Candida glabrata FKS1 and FKS2 mutations on echinocandin sensitivity and kinetics of 1,3-beta-D-glucan synthase: implication for the existing susceptibility breakpoint," Antimicrob Agents Chemother. 53(9):3690-3699 (2009).

(56) References Cited

OTHER PUBLICATIONS

GenBank Accesion No. AYN77793.1, "1,3-beta-D-glucan synthase [[*Candida*] auris]," <https:///www.ncbi.nlm.nih.gov/protein/AYN77793.1>, dated Oct. 30, 2018, retrieved Oct. 16, 2020 (2 pages).

Guo et al., "Synthesis and antifungal activities of glycosylated derivatives of the cyclic peptide fungicide caspofungin," ChemMedChem. 7(8):1496-503 (2012).

Heikkilä et al., "The prevalence of onychomycosis in Finland," Br J Dermatol. 133(5):699-703 (1995).

International Preliminary Report on Patentability for International Application No. PCT/US2013/031678, dated Sep. 23, 2014 (11 pages).

International Preliminary Report on Patentability for International Application No. PCT/US2017/022551, dated Sep. 27, 2018 (9 pages).

International Preliminary Report on Patentability for International Patent Application No. PCT/US2012/027451, dated Jan. 28, 2014 (7 pages).

International Search Report and Written Opinion for International Application No. PCT/US18/41617, dated Nov. 9, 2018 (16 pages).

International Search Report and Written Opinion for International Application No. PCT/US2012/027451, dated Jun. 20, 2012 (16 pages).

International Search Report and Written Opinion for International Application No. PCT/US2013/031678, dated Jun. 12, 2013 (19 pages).

International Search Report and Written Opinion for International Application No. PCT/US2016/052159, dated Jan. 13, 2017 (16 pages).

International Search Report and Written Opinion for International Application No. PCT/US2016/052165, dated Jan. 9, 2017 (25 pages).

International Search Report and Written Opinion for International Application No. PCT/US2017/012533, dated May 8, 2017 (15 pages).

International Search Report and Written Opinion for International Application No. PCT/US2017/022551, dated Jun. 12, 2017 (15 pages).

International Search Report and Written Opinion for International Application No. PCT/US2017/059046, dated Apr. 3, 2018 (14 pages).

International Search Report and Written Opinion for International Application No. PCT/US2017/063696, dated Feb. 1, 2018 (14 pages).

International Search Report and Written Opinion for International Application No. PCT/US2018/014883, dated Mar. 29, 2018 (16 pages).

International Search Report and Written Opinion for International Application No. PCT/US2018/016236, dated May 2, 2018 (13 pages).

International Search Report and Written Opinion for International Application No. PCT/US2018/026261, dated Jul. 20, 2018 (15 pages).

International Search Report and Written Opinion for International Application No. PCT/US2018/027614, dated Jun. 29, 2018 (16 pages).

Invitation to Pay Additional Fees for International Application No. PCT/US2018/041617, dated Sep. 14, 2018 (2 pages).

James et al., "Biafungin (CD101), a novel echinocandin, displays a long half-life in the chimpanzee, suggesting a once-weekly IV dosing option," 54th Interscience Conference on Antimicrobial Agents and Chemotherapy, Sep. 5-9, Washington D.C., Abstract A-694, retrieved from <http://n33px2pjph02hfyxt1xmwn4m.wpengine.netdna-cdn.com/wp-content/uploads/2014/12/A-694.-Biafungin-CD101-a-Novel-Echinocandin-Displays-a-Long-Half-life-in-the-Chimpanzee-Suggesting-a-Once-Weekly-IV-Dosing-Option.pdf> (2014) (2 pages).

James et al., "Structure-Activity Relationships of a Series of Echinocandins and the Discovery of CD101, a Highly Stable and Soluble Echinocandin with Distinctive Pharmacokinetic Properties," Antimicrob Agents Chemother. 61(2):e01541-16 (2017) (8 pages).

Jamison et al., "The synthesis and antifungal activity of nitrogen containing hemiaminal ethers of LY303366," J Antibiot (Tokyo). 51(2): 239-42 (1998).

Kathuria et al., "Multidrug-Resistant *Candida auris* Misidentified as *Candida haemulonii*: Characterization by Matrix-Assisted Laser Desorption Ionization-Time of Flight Mass Spectrometry and DNA Sequencing and Its Antifungal Susceptibility Profile Variability by Vitek 2, CLSI Broth Microdilution, and Etest Method," J Clin Microbiol. 53(6):1823-30 (2015).

Krishnan et al., "CD101, a novel echinocandin with exceptional stability properties and enhanced aqueous solubility," J Antibiot (Tokyo). 70(2):130-5 (2017).

Lakota et al., "Pharmacokinetic-Pharmacodynamic Target Attainment Analyses to Support the Selection of Extended-Interval CD101 Dosing Regimens," IDWeek 2016, Oct. 26-30, New Orleans, Louisiana. Poster No. 1994 (2016) (2 pages).

Lakota et al., "Pharmacological Basis of CD101 Efficacy: Exposure Shape Matters," Antimicrob Agents Chemother. 61(11):e00758-17 (2017) (7 pages).

Lee et al., "First Three Reported Cases of Nosocomial Fungemia Caused by *Candida auris*," J Clin Microbiol. 49(9):3139-42 (2011).

Locke et al., "Characterization of In Vitro Resistance Development to the Novel Echinocandin CD101 in *Candida* Species," Antimicrob Agents Chemother. 60(10):6100-6107 (2016).

Metzler et al., "Comparison of minimal inhibitory and mutant prevention drug concentrations of 4 fluoroquinolones against clinical isolates of methicillin-susceptible and -resistant *Staphylococcus aureus*," Int J Antimicrob Agents. 24(2):161-7 (2004).

Notice of Reasons for Rejection for Japanese Application No. 2018-036159, dated Nov. 12, 2019 (5 pages).

Office Action and English Translation for Chinese Application No. 201280021321.9, dated Nov. 16, 2015 (20 pages).

Office Action and English translation for Chinese Patent Application 201380026168.3, dated Sep. 15, 2015 (20 pages).

Office Action and English Translation for Russian Patent Application No. 2017128118, dated Jun. 17, 2019 (8 pages).

Office Action for U.S. Appl. No. 15/371,333, dated Sep. 29, 2017 (23 pages).

Ong et al., "A Single-Dose, Subcutaneous (SC) Prophylaxis CD101 Administration Prevents Fungal Infection in Mouse Models of Candidiasis and Aspergillosis," ASM Microbe, Jun. 1-5, New Orleans, Louisiana, Poster 241 (2017).

Ong et al., "Antifungal Prophylaxis with CD101 in Immunosuppressed Mouse Models of Candidiasis, Aspergillosis, and Pneumocystis Pneumonia (PCP)," European Hematology Association Congress, Jun. 22-25, Madrid, Spain, Poster P645 (2017).

Ong et al., "Efficacy of CD101, a Novel Echinocandin, In Mouse Models of Aspergillosis and Azole-Resistant Disseminated Candidiasis," ASH Annual Meeting, Dec. 3-6, San Diego, California, 3400 (2016).

Ong et al., "Pharmacokinetics of the Novel Echinocandin CD101 in Multiple Animal Species," Antimicrob Agents Chemother. 61(4):e01626-16 (2017) (8 pages).

Ong et al., "Preclinical Evaluation of the Stability, Safety, and Efficacy of CD101, a Novel Echinocandin," Antimicrob Agents Chemother. 60(11):6872-9 (2016).

Ong et al., "Prophylactic, Single-Dose, Subcutaneous (SC) Administration of CD101 Shows Robust Efficacy in Neutropenic Mouse Models of Candidiasis and Aspergillosis," European Congress of Clinical Microbiology and Infectious Diseases, Apr. 22-25, Vienna, Austria, EP0703 (2017).

Ong et al., "Subcutaneous (SC) Injection of CD101, a Novel Echinocandin: Efficacious, Well-Tolerated and Sustained Drug Exposures," International Immunocompromised Host Society-Infocus, Nov. 13-15, Santiago, Chile, poster (2016).

Partial supplementary European Search Report for European Patent Application No. 12751994.0, dated Mar. 10, 2015 (5 pages).

Pfaller et al., "Activity of a Long-Acting Echinocandin (CD101) and Seven Comparator Antifungal Agents Tested against a Global Collection of Contemporary Invasive Fungal Isolates in the SEN-

(56) References Cited

OTHER PUBLICATIONS

TRY 2014 Antifungal Surveillance Program," Antimicrob Agents Chemother. 61(3):e02045-16 (2017) (7 pages).

Pfaller et al., "Activity of a long-acting echinocandin, CD101, determined using CLSI and EUCAST reference methods, against *Candida* and *Aspergillus* spp., including echinocandin- and azole-resistant isolates," J Antimicrob Chemother. 71(10):2868-73 (2016).

Pfaller et al., "CD101, a long-acting echinocandin, and comparator antifungal agents tested against a global collection of invasive fungal isolates in the SENTRY 2015 Antifungal Surveillance Program," Int Journ Antimicrob Agents. 50(3):352-358 (2017).

Pfizer Inc., "Eraxis (anidulafungin) for Injection," <http://dailymed.nlm.nih.gov/dailymed/archives/fdaDrugInfo.cfm?archiveid=4744>, revised May 2007, retrieved on Oct. 1, 2015 (21 pages).

PubChem: Substance Record for SID 144216468, available Oct. 8, 2012, retrieved Feb. 9, 2017 (5 pages).

Rodriguez et al., "The Synthesis of Water Soluble Prodrugs Analogs of Echinocandin B," Bioorg Med Chem Lett. 9(13):1863-1868 (1999).

Sandison et al., "Pharmacokinetics, Safety, and Target Attainment of Single and Multiple Doses of CD101 IV—a Novel, Once-Weekly Echinocandin," 58th Annual Meeting of the American Society of Hematology, Dec. 5-8, San Diego, California. Abstract 2197 (2016) (1 page).

Sandison et al., "Safety and Pharmacokinetics of CD101 IV, a Novel Echinocandin, in Healthy Adults," Antimicrob Agents Chemother. 61(2):e01627-16 (2017) (11 pages).

Sandison et al., "Safety and Pharmacokinetics of Multiple Doses of CD101 IV: Results From a Phase 1, Dose-Escalation Study," ASM Microbe 2016, Jun. 16-20, Boston, Massachusetts. Abstract LB-057 (2016) (1 page).

Sandison et al., "Safety and Pharmacokinetics of Single and Multiple Doses of CD101 IV: Results from Two Phase 1 Dose-Escalation Studies," 19th Immunocompromised Host Society Symposium, 14th Forum on Fungal Infection in the Clinical Practice, Nov. 13-15, Santiago, Chile (2016) (1 page).

Sandison et al., "Safety and Pharmacokinetics of Single and Multiple Doses of CD101 IV: Results from Two Phase 1 Dose-Escalation Studies," 2016 American College of Clinical Pharmacy Annual Meeting, Oct. 23-26, Hollywood, Florida. Poster 258 (2016) (1 page).

Sandison, "CD101: A Novel Echinocandin," Trends in Medical Mycology, Oct. 6-9, Belgrade, Serbia, presentation (2017) (16 pages).

Strickley, "Solubilizing excipients in oral and injectable formulations," Pharm Res. 21(2):201-30 (2004).

Thye, "The safety and single-dose pharmacokinetics of CD101 IV: results from a phase 1, dose-escalation study," 26th European Congress of Clinical Microbiology and Infectious Diseases, Amsterdam, Netherlands, Apr. 9-12, 2016. Retrieved from <http://www.cidara.com/wp-content/uploads/2016/04/The-safety-and-single-dose-pharmacokinetics-of-CD101-IV-results-from-a-phase-1-dose-escalation-study.pdf> (12 pages).

Uzun et al., "In vitro activity of a new echinocandin, LY303366, compared with those of amphotericin B and fluconazole against clinical yeast isolates," Antimicrob Agents Chemother. 41(5): 1156-7 (1997).

Verweij et al., "Efficacy of LY303366 against amphotericin B-susceptible and -resistant *Aspergillus fumigatus* in a murine model of invasive aspergillosis," Antimicrob Agents Chemother. 42(4): 873-78 (1998).

Walpole et al., "The weight of nations: an estimation of adult human biomass," BMC Public Health. 12:439 (2012) (6 pages).

Wang et al., "Medical Organic Chemistry," Shandong People's Publishing House, 192 (2015) (2 pages).

Yasuhara et al., "Pharmacokinetics for Primers," Japanese Journal of Clinical Pharmacology and Therapeutics. 41(4):155-158 (2010) (9 pages).

Zhang et al., "Fundamentals of Medical Chemistry," People's Military Medical Press, 108 (2015) (2 pages).

Zhao et al., "CD101: a novel long-acting echinocandin," Cell Microbiol. 18(9):1308-16 (2016).

Zhao et al., "Unraveling Drug Penetration of Echinocandin Antifungals at the Site of Infection in an Intra-abdominal Abscess Model," Antimicrob Agents Chemother. 61(10):e01009-17 (2017) (13 pages).

Zhao et al., "Unraveling Drug Penetration of Echinocandin Antifungals at the Site of Infection in an Intra-abdominal Abscess Model," manuscript available on Jul. 24, 2017, published in final edited form as: Antimicrob Agents Chemother. 61(10): e01009-17. doi:10.1128/AAC.01009-17 (2017) (34 pages).

Zimbeck et al., "FKS mutations and elevated echinocandin MIC values among *Candida glabrata* isolates from U.S. population-based surveillance," Antimicrob Agents Chemother. 54(12):5042-47 (2010).

Ceballos et al., "Successful treatment with echinocandin in an HIV-infected individual failing first-line therapy for *Pneumocystis jirovecii* pneumonia," AIDS. 25(17):2192-3 (Nov. 13, 2011).

Highlights of Prescribing Information for ERAXIS™, Pfizer, Nov. 2013 (17 pages).

\* cited by examiner

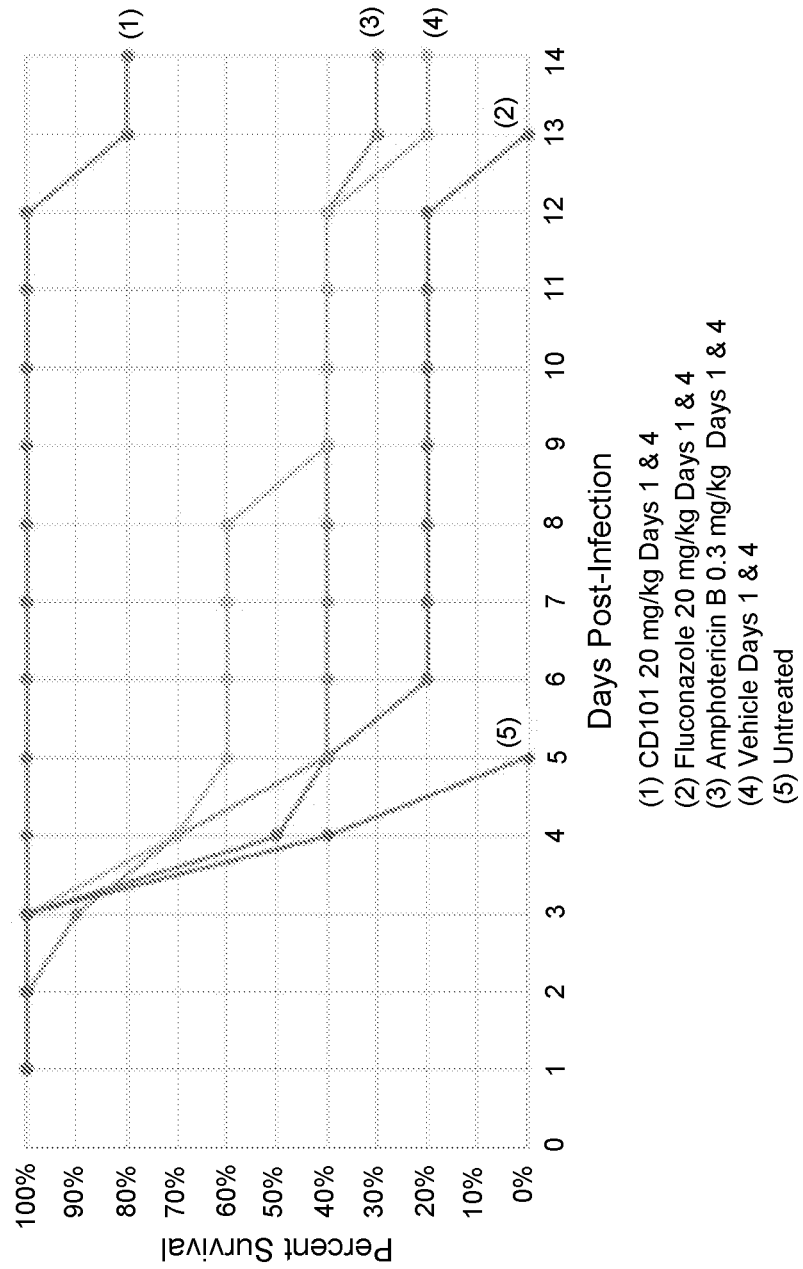

* P-value compared to untreated control.

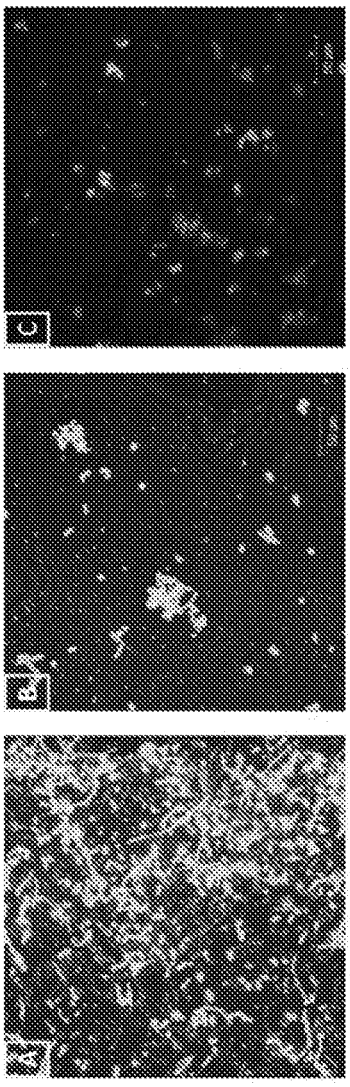
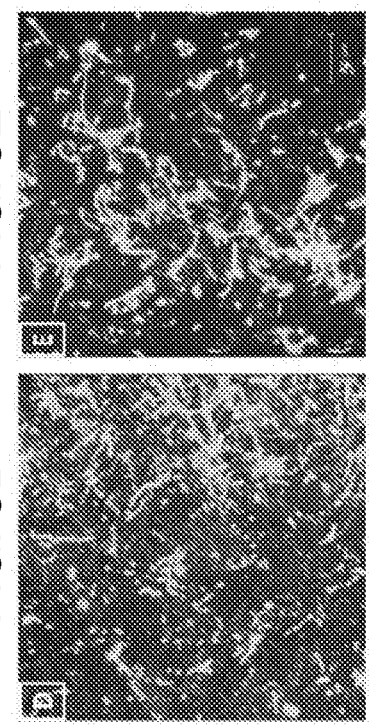

* P- value compared to untreated control.

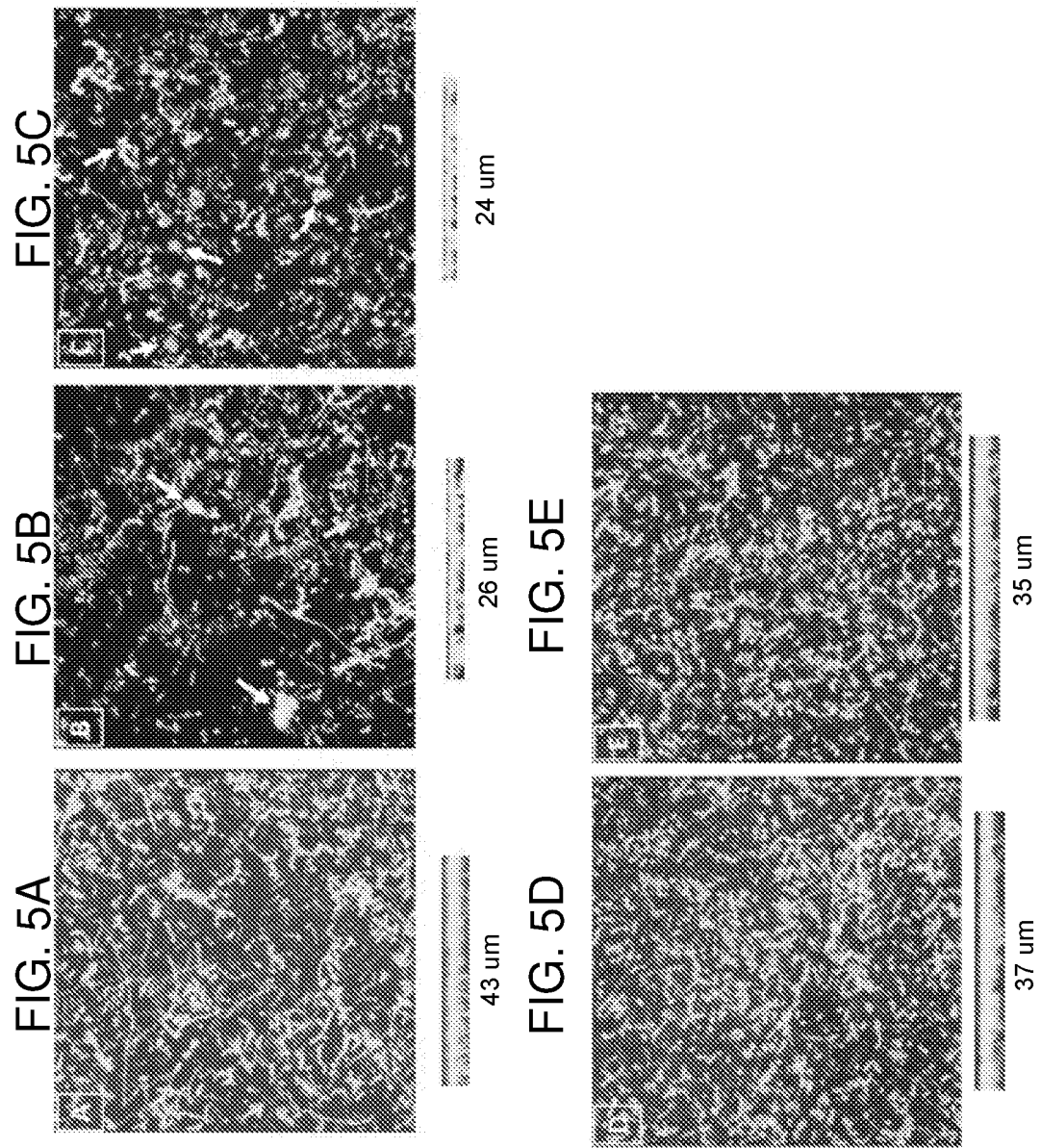

* P- value compared to untreated control.

16h

0h

0h

16h

0h

16h

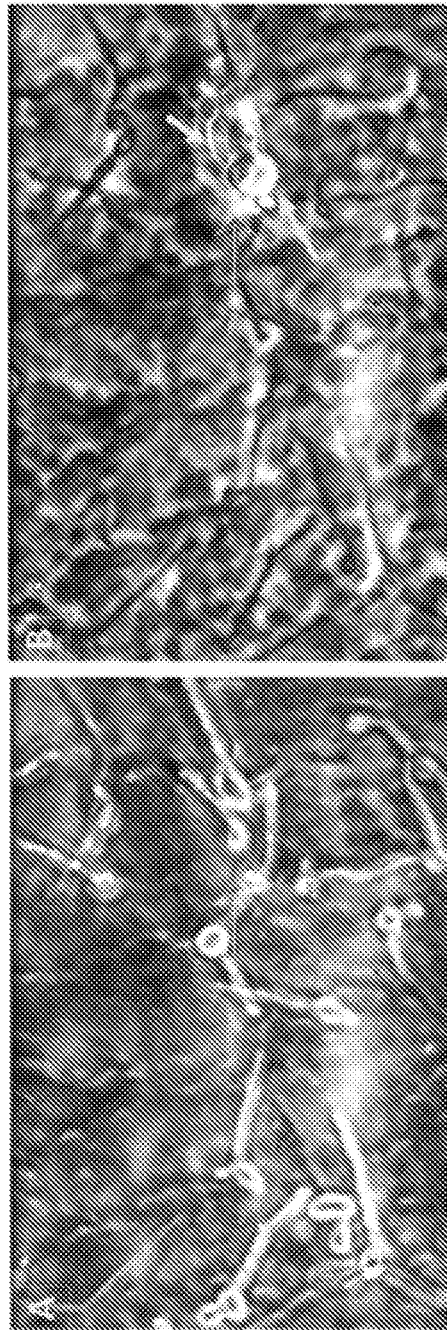

COMPOSITIONS AND METHODS FOR THE TREATMENT OF FUNGAL INFECTIONS

BACKGROUND

The disclosure relates to the field of treatment of fungal infections. Systemic infections caused by *Candida* are serious and life-threatening infections that represent a significant public health issue, particularly in highly vulnerable patient populations such as the elderly, post-surgical, critically ill, and other hospitalized patients with serious medical conditions. The Centers for Disease Control and Prevention recently warned that fluconazole-resistant *Candida* have the potential to pose a serious threat to public health. However, since 2007, no new antifungal agents have been approved for treatment of candidemia. There is an urgent need to develop new and more effective treatments of *Candida* and other fungal infections.

SUMMARY OF THE DISCLOSURE

The disclosure relates to compositions and methods for the treatment of fungal infections. In particular, we have discovered pharmaceutical compositions for intravenous administration of CD101 (e.g., in salt or neutral form) that exhibit reduced local irritation upon intravenous administration to a subject. CD101 is a broad-spectrum antifungal agent with excellent activity against fungal species, e.g., *Candida* spp. and *Aspergillus* spp.

In a first aspect is a pharmaceutical composition for intravenous injection including an aqueous solution including at least 85% (w/w) water, between 0.4 mg/mL and 10 mg/mL CD101 (e.g., between 0.4 mg/mL and 9 mg/mL, between 0.4 mg/mL and 8 mg/mL, between 0.4 mg/mL and 7 mg/mL, between 0.4 mg/mL and 6 mg/mL, between 0.4 mg/mL and 5 mg/mL, between 0.4 mg/mL and 4 mg/mL, between 0.4 mg/mL and 3 mg/mL, between 0.4 mg/mL and 2 mg/mL, between 0.4 mg/mL and 1 mg/mL, between 0.6 mg/mL and 10 mg/mL, between 0.7 mg/mL and 10 mg/mL, between 0.8 mg/mL and 10 mg/mL, between 0.9 mg/mL and 10 mg/mL, between 1 mg/mL and 10 mg/mL, between 2 mg/mL and 10 mg/mL, between 3 mg/mL and 10 mg/mL, between 4 mg/mL and 10 mg/mL, between 5 mg/mL and 10 mg/mL, between 6 mg/mL and 10 mg/mL, between 7 mg/mL and 10 mg/mL, between 8 mg/mL and 10 mg/mL, or between 9 mg/mL and 10 mg/mL CD101; about 0.4 mg/mL, about 0.6 mg/mL, about 0.8 mg/mL, about 1 mg/mL, about 1.2 mg/mL, about 1.4 mg/mL, about 1.6 mg/mL, about 1.8 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, or about 10 mg/mL CD101), and an intravenous solubility promoter, wherein the weight to weight (w/w) ratio of the intravenous solubility promoter to the CD101 in the pharmaceutical composition is at least 2 (e.g., between 2 and 8, e.g., 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, or 8), the CD101 is in its salt or neutral form, the pharmaceutical composition has a pH of between 5 and 7 (e.g., 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, or 7), and the pharmaceutical composition exhibits reduced local irritation upon intravenous administration to a subject.

In some embodiments of this aspect, the w/w ratio of the intravenous solubility promoter to the CD101 in the pharmaceutical composition is between 2 and 8 (e.g., 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, or 8). In some embodiments of this aspect, the concentration of CD101 in the pharmaceutical composition is between 0.4 mg/mL and 4 mg/mL (e.g., about 0.8 mg/mL (e.g., 0.8±0.2 mg/mL) or about 1.6 mg/mL (e.g., 1.6±0.2 mg/mL)).

In a second aspect is a pharmaceutical composition including an effective amount of CD101 and an intravenous solubility promoter in a lyophilized composition, wherein the weight to weight (w/w) ratio of the intravenous solubility promoter to the CD101 in the lyophilized composition is between 2 and 8 (e.g., 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, or 8), the CD101 is in its salt or neutral form, and the lyophilized composition, once reconstituted, provides an aqueous solution having a pH of between 5 and 7 (e.g., 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, or 7).

In some embodiments, the intravenous solubility promoter is selected from the group consisting of polysorbate 20 (Tween 20; polyoxyethylene (20) sorbitan monolaurate), polysorbate 40 (Tween40; polyoxyethylene (40) sorbitan monopalmitate), polysorbate 60 (Tween 60; polyoxyethylene (60) sorbitan monostearate), polysorbate 80 (Tween 80; polyoxyethylene (80) sorbitan monooleate), β-cyclodextrin, polyoxyl 35 castor oil (Cremophor EL), polyoxyl 40 hydrogenated castor oil (Cremophor RH 40), polyoxyl 60 hydrogenated castor oil (Cremophor RH 60), D-α-tocopheryl polyethylene glycol 1000 succinate (TPGS), sorbitan monooleate (Span 20), polyoxyl 8 stearate (PEG 400 monosterate), polyoxyl 40 stearate (PEG 1750 monosterate), PEG 400 caprylic/capric glycerides (Labrasol), PEG 300 oleic glycerides (Labrafil M-1944CS), phosphatidylcholine (lecithin), alkylglucoside, sucrose monolaurate, sucrose monooleate, and polyoxyethylene-polyoxypropylene block copolymer (Poloxamer). In some embodiments, the alkylglucoside is an alkyl monoglucoside (e.g., hexylglucoside, heptaglucoside, octylglucoside, nonaglucoside, decylglucoside, dodecylglucoside, or tetradecylglucoside). In some embodiments, the alkylglucoside is an alkyl diglucoside (e.g., hexylmaltoside, heptamaltoside, octylmaltoside, nonamaltoside, decylmaltoside, dodecylmaltoside (e.g., dodecyl-β-D-maltoside (DDM)), or tetradecylmaltoside (e.g., tetradecyl-β-D-maltoside (TDM))).

In some embodiments, the intravenous solubility promoter is polysorbate 80 (Tween 80; polyoxyethylene (80) sorbitan monooleate).

In some embodiments of the first two aspects of the invention, the pharmaceutical composition further includes a buffer. In some embodiments, the buffer is histidine, citrate, succinate, lactate, propanoate, arginine, tris(hydroxymethyl)aminomethane (tris), glycine, acetate, or formate. In some embodiments of the first two aspects of the invention, the buffer includes monovalent molecules (e.g., acetate, lactate, formate, histidine, tris(hydroxymethyl)aminomethane (tris), arginine, and/or glycine). In some embodiments of the first two aspects of the invention, the buffer includes amino acids (e.g., histidine, arginine, and/or glycine).

In some embodiments of the first aspect of the invention, the pharmaceutical composition further includes between 0.12% and 0.6% (w/w) of a saccharide (e.g., between 0.12% and 0.58% (w/w), between 0.12% and 0.56% (w/w), between 0.12% and 0.54% (w/w), between 0.12% and 0.52% (w/w), between 0.12% and 0.5% (w/w), between 0.12% and 0.48% (w/w), between 0.12% and 0.46% (w/w), between 0.12% and 0.44% (w/w), between 0.12% and 0.42% (w/w), between 0.12% and 0.4% (w/w), between 0.12% and 0.38% (w/w), between 0.12% and 0.36% (w/w), between 0.12% and 0.34% (w/w), between 0.12% and 0.32% (w/w), between 0.12% and 0.3% (w/w), between 0.12% and 0.28% (w/w), between 0.12% and 0.26% (w/w), between 0.12% and 0.24% (w/w), between 0.12% and 0.22% (w/w), between 0.12% and 0.2% (w/w), between 0.12% and 0.18% (w/w), between 0.12% and 0.16% (w/w), or between 0.12% and 0.14% (w/w) of a saccharide; about 0.12% (w/w), about 0.14% (w/w), about 0.16% (w/w), about 0.18% (w/w), about 0.2% (w/w), about 0.22% (w/w), about 0.24% (w/w), about 0.26% (w/w), about 0.28% (w/w), about 0.3% (w/w), about 0.32% (w/w), about 0.34% (w/w), about 0.36% (w/w), about 0.38% (w/w), about 0.4% (w/w), about 0.42% (w/w), about 0.44% (w/w), about 0.46% (w/w), about 0.48% (w/w), about 0.5% (w/w), about 0.52% (w/w), about 0.54% (w/w), about 0.56% (w/w), about 0.58% (w/w), or about 0.6% (w/w) of a saccharide). In some embodiments, the saccharide is mannitol, sucrose, trehalose, maltose, dextrose, or lactose (e.g., mannitol).

In some embodiments of the second aspect of the invention, the pharmaceutical composition further includes between 2% and 10% (w/w) of a saccharide (e.g., between 2% and 9% (w/w), between 2% and 8% (w/w), between 2% and 7% (w/w), between 2% and 6% (w/w), between 2% and 5% (w/w), between 2% and 4% (w/w), or between 2% and 3% (w/w) of a saccharide; about 2% (w/w), about 3% (w/w), about 4% (w/w), about 5% (w/w), about 6% (w/w), about 7% (w/w), about 8% (w/w), about 9% (w/w), or about 10% (w/w) of a saccharide).

In some embodiments, the CD101 in salt form in pharmaceutical compositions and methods described herein is CD101 acetate.

In another aspect is a method of treating or preventing a fungal infection in a subject by intravenously administering the pharmaceutical composition of the first aspect of the invention to the subject, wherein the method exhibits reduced local irritation upon intravenous administration of the pharmaceutical composition to a subject.

In another aspect is a method of treating or preventing a fungal infection in a subject by: (i) reconstituting the pharmaceutical composition of the second aspect of the invention to form an aqueous solution; and (ii) intravenously administering the aqueous solution to the subject, wherein the concentration of the CD101 in the aqueous solution is between 0.4 mg/mL and 10 mg/mL (e.g., between 0.4 mg/mL and 9 mg/mL, between 0.4 mg/mL and 8 mg/mL, between 0.4 mg/mL and 7 mg/mL, between 0.4 mg/mL and 6 mg/mL, between 0.4 mg/mL and 5 mg/mL, between 0.4 mg/mL and 4 mg/mL, between 0.4 mg/mL and 3 mg/mL, between 0.4 mg/mL and 2 mg/mL, between 0.4 mg/mL and 1 mg/mL, between 0.6 mg/mL and 10 mg/mL, between 0.7 mg/mL and 10 mg/mL, between 0.8 mg/mL and 10 mg/mL, between 0.9 mg/mL and 10 mg/mL, between 1 mg/mL and 10 mg/mL, between 2 mg/mL and 10 mg/mL, between 3 mg/mL and 10 mg/mL, between 4 mg/mL and 10 mg/mL, between 5 mg/mL and 10 mg/mL, between 6 mg/mL and 10 mg/mL, between 7 mg/mL and 10 mg/mL, between 8 mg/mL and 10 mg/mL, or between 9 mg/mL and 10 mg/mL CD101; about 0.4 mg/mL, about 0.6 mg/mL, about 0.8 mg/mL, about 1 mg/mL, about 1.2 mg/mL, about 1.4 mg/mL, about 1.6 mg/mL, about 1.8 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, or about 10 mg/mL CD101), the CD101 is in its salt or neutral form, and the method exhibits reduced local irritation upon intravenous administration of the aqueous solution to a subject.

In some embodiments of this aspect, the concentration of CD101 in the pharmaceutical composition is about 0.4 mg/mL. In some embodiments of this aspect, the concentration of CD101 in the pharmaceutical composition is about 0.8 mg/mL. In some embodiments, the concentration of CD101 in the pharmaceutical composition is about 1.6 mg/mL.

In some embodiments of this aspect, the concentration of CD101 in the pharmaceutical composition is about 3.0 mg/mL. In some embodiments, the concentration of CD101 in the pharmaceutical composition is about 4.0 mg/mL.

In some embodiments of the methods of the invention, the method includes intravenously administering to the subject by infusion. In some embodiments, the method includes intravenously administering to the subject by infusion at a constant infusion rate of between 2 mL/minute and 9 mL/minute (e.g., between 2 mL/minute and 8 mL/minute, between 2 mL/minute and 7 mL/minute, between 2 mL/minute and 6 mL/minute, between 2 mL/minute and 5 mL/minute, between 2 mL/minute and 4 mL/minute, between 2 mL/minute and 3 mL/minute, between 3 mL/minute and 9 mL/minute, between 4 mL/minute and 9 mL/minute, between 5 mL/minute and 9 mL/minute, between 6 mL/minute and 9 mL/minute, between 7 mL/minute and 9 mL/minute, or between 8 mL/minute and 9 mL/minute; e.g., 2, 2.5, 3, 3.5, 4, 4.5, 5, 5.5, 6, 6.5, 7, 7.5, 8, 8.5, or 9 mL/minute). In some embodiments, the method includes intravenously administering to the subject by infusion over 30 to 120 minutes (e.g., 30, 40, 50, 60, 70, 80, 90, 100, 110, or 120 minutes).

In some embodiments of the methods of the invention, the method includes intravenously administering at least one dose every 5 to 15 days (e.g., every 5, 6, 7, 8, 9, 10, 11, 12, 13, 14, or 15 days). In some embodiments, the method includes intravenously administering one dose every 5 to 15 days (e.g., every 5, 6, 7, 8, 9, 10, 11, 12, 13, 14, or 15 days).

In some embodiments of the methods of the invention, the fungal infection to be treated or prevented is selected from candidemia, invasive candidiasis, *Tinea capitis, Tinea corporis, Tinea pedis*, onychomycosis, perionychomycosis, *Pityriasis versicolor*, oral thrush, vaginal candidiasis, respiratory tract candidiasis, biliary candidiasis, eosophageal candidiasis, urinary tract candidiasis, systemic candidiasis, mucocutaneous candidiasis, aspergillosis, mucormycosis, paracoccidioidomycosis, North American blastomycosis, histoplasmosis, coccidioidomycosis, sporotrichosis, fungal sinusitis, or chronic sinusitis. In some embodiments, the infection is candidemia or invasive candidiasis.

In some embodiments of the methods of the invention, the fungal infection to be treated or prevented is an infection of *Candida albicans, C. glabrata, C. dubliniensis, C. krusei, C. parapsilosis, C. tropicalis, C. orthopsilosis, C. guilliermondii, C. rugosa, C. auris, C. lusitaniae, Aspergillus fumigatus, A. flavus, A. terreus, A. niger, A. candidus, A. clavatus*, or *A. ochraceus*.

In another aspect, the invention features a method of preventing or treating a biofilm in a subject. The method includes administering to the subject a pharmaceutical composition comprising CD101 salt, or a neutral form thereof, and one or more pharmaceutically acceptable excipients.

In some embodiments of this aspect, the biofilm in the subject is a *Candida* biofilm (e.g., *Candida albicans* biofilm). In some embodiments, the biofilm is attached to a mucous membrane of the subject.

In another aspect, the invention features a method of preventing biofilm growth on a catheter or killing a biofilm attached to a catheter comprising submerging the catheter in an aqueous solution comprising CD101 salt, or a neutral form thereof, or running an aqueous solution comprising CD101 salt, or a neutral form thereof, through the lumen of the catheter.

In some embodiments of this aspect, the biofilm on the catheter is a *Candida* biofilm (e.g., *Candida albicans* biofilm).

Definitions

The terms "intravenous administration" or "intravenously administering," as used herein, refer to intravenous infusion of a drug to a subject.

The term "fungal infection," as used herein, refers to the invasion of a subject's cells, tissues, and/or organs by fungi (e.g., *Candida* spp. or *Aspergillus* spp.), thus, causing an infection. In some embodiments, the fungi may grow, multiply, and/or produce toxins in the subject's cells, tissues, and/or organs. In some embodiments, a fungal infection can be any situation in which the presence of a fungal population(s) is latent within or damaging to a host body. Thus, a subject is "suffering" from a fungal infection when a latent fungal population is detectable in or on the subject's body, an excessive amount of a fungal population is present in or on the subject's body, or when the presence of a fungal population(s) is damaging the cells, tissues, and/or organs of the subject.

The term "protecting against a fungal infection" or "preventing a fungal infection" as used herein, refers to preventing a subject from developing a fungal infection or decreasing the risk that a subject may develop a fungal infection (e.g., a fungal infection caused by *Candida* spp. or *Aspergillus* spp.). Prophylactic drugs used in methods of protecting against a fungal infection in a subject are often administered to the subject prior to any detection of the fungal infection. In some embodiments of methods of protecting against a fungal infection, a subject (e.g., a subject at risk of developing a fungal infection) may be administered a pharmaceutical composition of the invention to prevent the fungal infection development or decrease the risk of the fungal infection development.

As used herein, the term "biofilm" refers to a three-dimensional structure composed of heterogeneous fungi (e.g., *Candida*) and hyphae that can attach to various surfaces, e.g., a mucous membrane or the inside of a catheter. Biofilms can form on the surfaces of medical devices and cause biofilm device-associated infections. For example, having a biofilm on an indwelling device, e.g., a vascular catheter, can cause life-threatening infections.

The term "treating" or "to treat," as used herein, refers to a therapeutic treatment of a fungal infection (e.g., a fungal infection caused by *Candida* spp. or *Aspergillus* spp.) in a subject. In some embodiments, a therapeutic treatment may slow the progression of the fungal infection, improve the subject's outcome, and/or eliminate the infection. In some embodiments, a therapeutic treatment of a fungal infection (e.g., a fungal infection caused by *Candida* spp. or *Aspergillus* spp.) in a subject may alleviate or ameliorate of one or more symptoms or conditions associated with the fungal infection, diminish the extent of the fungal infection, stabilize (i.e., not worsening) the state of the fungal infection, prevent the spread of the fungal infection, and/or delay or slow the progress of the fungal infection, as compare the state and/or the condition of the fungal infection in the absence of therapeutic treatment.

The term "local irritation," as used herein, refers to any adverse reactions the subject might experience at the site of the intravenous injection after a drug is administered. Local irritations at the injection site may include, e.g., pain or tenderness at the injection site, itching, bruising, and/or swelling of the skin, venous discoloration (e.g., darkening of the blood vein leading away from the site of injection), and skin rash. "Reduced local irritation" refers to diminished local irritation or no local irritation observed when intravenously administering a pharmaceutical composition of the invention to a subject, relative the irritation observed when intravenously administering other compositions.

The term "intravenous solubility promoter," as used herein, refers to an agent that promotes the intravenous solubility of CD101 (e.g., CD101 in salt or neutral form) in the bloodstream of a subject once the pharmaceutical composition is intravenously administered. The intravenous precipitation of CD101 can cause local irritations at the site of injection (e.g., pain or tenderness at the injection site, itching, bruising, and/or swelling of the skin, venous discoloration (e.g., darkening of the blood vein leading away from the site of injection), and skin rash). The intravenous solubility promoter in a pharmaceutical composition of the invention functions to decrease the intravenous precipitation of CD101 (e.g., CD101 in salt or neutral form) in the bloodstream of a subject relative the intravenous precipitation of CD101 if it was in a composition without the intravenous solubility promoter. In some embodiments, a pharmaceutical composition of the invention contains polysorbate 80 (Tween 80) as the intravenous solubility promoter.

The term "alkylglucoside," as used herein, refers to a surfactant having an alkyl chain (e.g., an alkyl chain ranging from six to 18 carbon atoms) conjugated to one or more glucose molecules. An alkylglucoside may be an alkyl monoglucoside (e.g., an alkyl chain conjugated to one glucose molecule) or an alkyl diglucoside (e.g., an alkyl chain conjugated to a disaccharide containing two glucose molecules linked through an interglycosidic bond (e.g., maltose)).

The term "immunocompromised," as used herein, refers to a subject (e.g., a human) having a weakened immune system. The subject's immune system can be weakened or compromised by a disease (e.g., an HIV infection, an autoimmune disease, cancer), a medical procedure (e.g., an organ transplant (e.g., a solid organ transplant) or a bone marrow transplant), a drug (e.g., an immunosuppressant), and/or a pathogen (e.g., bacteria, fungus, virus). The immune system of the host may also have a congenital defect that renders the host more susceptible to infection.

The term "immunosuppression therapy," as used herein, refers to a therapy that uses one or more immunosuppressants to reduce the activation and/or efficacy of the immune system of a subject (e.g., a human). In some embodiments, an immunosuppression therapy is used to prevent the body from rejecting a transplant (e.g., an organ transplant (e.g., a solid organ transplant) or a bone marrow transplant), to treat graft-versus-host disease after a bone marrow transplant, and/or to treat autoimmune diseases (e.g., systemic lupus erythematosus, rheumatoid arthritis, Crohn's disease, multiple sclerosis, myasthenia gravis, Sarcoidosis, Behcet's disease). Immunosuppressants include, but are not limited to, calcineurin inhibitors, mTOR inhibitors, and tyrosine kinase inhibitors (e.g., cyclosporine A, cyclosporine G, voclosporin, tacrolimus, pimecrolimus, sirolimus, temsirolimus, deforolimus, everolimus, zotarolimus, biolimus, imatinib, dasatinib, nilotinib, erlotinib, sunitinib, gefitinib, bosutinib, neratinib, axitinib, crizotinib, lapatinib, toceranib and vatalanib).

The term "effective amount," as used herein, is meant the amount of drug required to treat or prevent an infection or a disease associated with an infection. The effective amount of drug used to practice the methods described herein for therapeutic or prophylactic treatment of conditions caused by or contributed to by a microbial infection varies depending upon the manner of administration, the age, body weight, and general health of the subject. Ultimately, the attending physician will decide the appropriate amount and dosage regimen. Such amount is referred to as an "effective amount."

The term "CD101 salt," as used herein, refers to a salt of the compound of Formula 1. CD101 has a structure (below) in which the tertiary ammonium ion positive charge of CD101 is balanced with a negative counterion (e.g., an acetate) in its salt form.

The term "CD101 neutral form," as used herein, includes the zwitterionic forms of CD101 in which the compound of Formula 1 has no net positive or negative charge. The zwitterion is present in a higher proportion in basic medium (e.g., pH 9) relative to CD101 or a salt of CD101. In some embodiments, the zwitterion may also be present in its salt form.

The term "concentration of CD101," as used herein, is calculated based on the molecular weight of CD101 as shown in Formula 1, not including the negative counterion (e.g., an acetate) if CD101 is in its salt form. For example, in some embodiments of the invention, the concentration of CD101 in the pharmaceutical composition is between 0.4 mg/mL and 4 mg/mL (e.g., about 0.8 mg/mL (e.g., 0.8±0.2 mg/mL) or about 1.6 mg/mL (e.g., 1.6±0.2 mg/mL)). These concentrations are calculated based on the molecular weight of CD101 as shown in Formula 1.

The term "weight to weight (w/w) ratio," as used herein, is calculated based on the molecular weight of CD101 as shown in Formula 1, not including the negative counterion (e.g., an acetate) if CD101 is in its salt form. For example, in some embodiments of the invention, the weight to weight (w/w) ratio of the blood solubilizing agent to CD101 in the pharmaceutical composition is at least 2 (e.g., between 2 and 8, e.g., 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, or 8). The w/w ratio of the blood solubilizing agent to CD101 is calculated based on the molecular weight of CD101 as shown in Formula 1.

The term "salt," as used herein, refers to any pharmaceutically acceptable salt, such as a non-toxic acid addition salt, metal salt, or metal complex, commonly used in the pharmaceutical industry. Examples of acid addition salts include organic acids, such as acetic, lactic, palmoic, maleic, citric, cholic acid, capric acid, caprylic acid, lauric acid, glutaric, glucuronic, glyceric, glycocolic, glyoxylic, isocitric, isovaleric, lactic, malic, oxalo acetic, oxalosuccinic, propionic, pyruvic, ascorbic, succinic, benzoic, palmitic, suberic, salicylic, tartaric, methanesulfonic, toluenesulfonic, and trifluoroacetic acids, and inorganic acids, such as hydrochloric acid, hydrobromic acid, sulfuric acid, and phosphoric acid. Representative alkali or alkaline earth metal salts include sodium, lithium, potassium, calcium, and magnesium, among others.

The term "dose," as used herein, is meant the amount of CD101 administered to the subject. As used herein, the amount in each dose refers to the amount of CD101 (Formula 1 shown above) that does not include the negative counterion (e.g., an acetate) if CD101 is in its salt form.

The term "between," as used herein, refers to any quantity within the range indicated and enclosing each of the ends of the range indicated. For example, a pH of between 5 and 7 refers to any quantity within 5 and 7, as well as a pH of 5 and a pH of 7.

The term "subject" or "patient," as used herein, is meant a human.

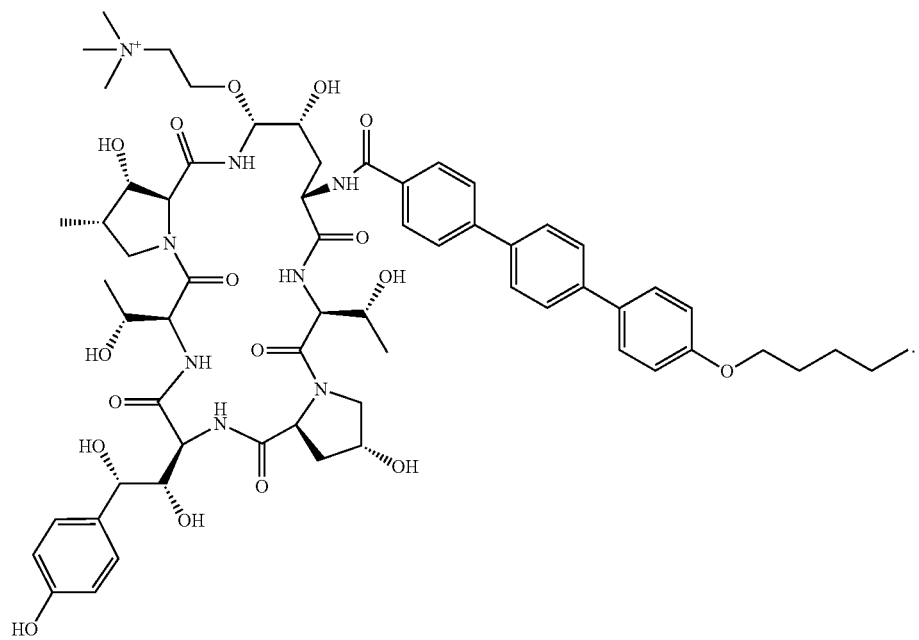

(Formula 1)

Other than in the operating examples, or where otherwise indicated, all numbers expressing quantities of ingredients, concentrations, or reaction conditions used herein should be understood as modified in all instances by the term "about." As used herein, the term "about" indicates a deviation of ±10%. For example, about 10% refers to from 9.5% to 10.5%. The term "about," as used herein, indicates a deviation of ±10%. For example, about 10% refers to from 9% to 11%.

Other features and advantages of the disclosure will be apparent from the following detailed description and the claims.

BRIEF DESCRIPTION OF THE DRAWINGS

FIG. 1 is a graph showing percent survival over time in mice infected with *Candida auris* and treated with 20 mg/kg CD101 (IP), 20 mg/kg fluconazole (PO), or 0.3 mg/kg amphotericin B (IP).

FIGS. 3A-3E are confocal scanning laser micrographs showing the effect of CD101 and fluconazole on adhesion phase *C. albicans* biofilms (prevention): top-down three-dimensional view (top panels) and side-views (bottom panels) of biofilms formed by *C. albicans* treated with: no drug (control;

FIG. 3A), 0.25 1 μg/ml CD101 (FIG. 3B), 1 μg/ml CD101 (FIG. 3C), 1 μg/ml fluconazole (FIG. 3D), and 4 μg/ml fluconazole (FIG. 3E).

FIGS. 5A-5E are confocal scanning laser micrographs showing the effect of CD101 and Fluconazole on Mature phase *C. albicans* Biofilms (treatment): Top-down three-dimensional view (top panels) and side-view (bottom panels) of biofilms exposed to: no drug (FIG. 5A), 0.25 μg/ml CD101 (FIG. 5B), 1 μg/ml CD101 (FIG. 5C), 1 μg/ml fluconazole (FIG. 5D), and 4 μg/ml fluconazole (FIG. 5E). Arrows show bulged/broken cells.

FIGS. 7A and 7B are images showing the temporal effect of CD101 (0.25 μg/ml) on 3 h formed *C. albicans* Biofilms. CD101 was added after 3 h biofilm formation and images were captured immediately after adding CD101 (FIG. 7A) and followed up to 16 h (FIG. 7B), magnification, ×63. Arrows show bulging, deformed, and broken cells.

DETAILED DESCRIPTION

Figure 2A:
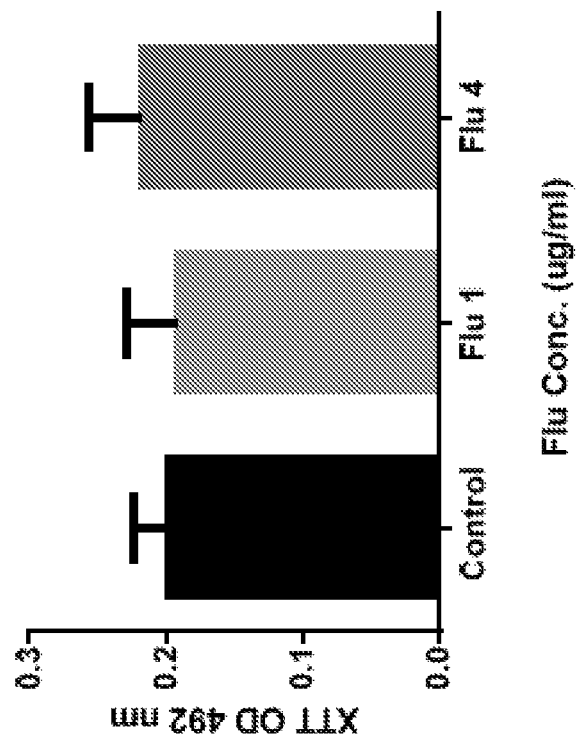
FIGS. 2A and 2B are bar graphs showing the effect of CD101 (0.25 or 1 μg/ml) (FIG. 2A) and fluconazole (1 or 4 μg/ml) (FIG. 2B) on metabolic activity of adhesion phase *C. albicans* biofilms compared to untreated control.

Provided are methods of treating a fungal infection in a subject in need thereof by intravenously administering to the subject CD101 (e.g., CD101 in salt or neutral form) formulated as an aqueous composition.

Pharmaceutical Compositions

CD101 is a semi-synthetic echinocandin that inhibits the synthesis of 1,3-β-D-glucan, an essential component of the fungal cell wall of yeast forms of *Candida* species and regions of active cell growth of *Aspergillus* hyphae. The synthesis of 1,3-β-D-glucan is dependent upon the activity of 1,3-β-D-glucan synthase, an enzyme complex in which the catalytic subunit is encoded by FKS1, FKS2, and FKS3 genes. Inhibition of this enzyme results in rapid, concentration-dependent, fungicidal activity for *Candida* spp. The structure of CD101 is depicted above.

The disclosure features pharmaceutical compositions for intravenous administration of CD101 (e.g., CD101 in salt or neutral form) to a subject. In some embodiments, the pharmaceutical composition for intravenous administration includes between 0.4 mg/mL and 10 mg/mL CD101 (e.g., between 0.4 mg/mL and 9 mg/mL, between 0.4 mg/mL and 8 mg/mL, between 0.4 mg/mL and 7 mg/mL, between 0.4 mg/mL and 6 mg/mL, between 0.4 mg/mL and 5 mg/mL, between 0.4 mg/mL and 4 mg/mL, between 0.4 mg/mL and 3 mg/mL, between 0.4 mg/mL and 2 mg/mL, between 0.4 mg/mL and 1 mg/mL, between 0.6 mg/mL and 10 mg/mL, between 0.7 mg/mL and 10 mg/mL, between 0.8 mg/mL and 10 mg/mL, between 0.9 mg/mL and 10 mg/mL, between 1 mg/mL and 10 mg/mL, between 2 mg/mL and 10 mg/mL, between 3 mg/mL and 10 mg/mL, between 4 mg/mL and 10 mg/mL, between 5 mg/mL and 10 mg/mL, between 6 mg/mL and 10 mg/mL, between 7 mg/mL and 10 mg/mL, between 8 mg/mL and 10 mg/mL, or between 9 mg/mL and 10 mg/mL CD101) and an intravenous solubility promoter.

The intravenous solubility promoter functions to promote the intravenous solubility of CD101 (e.g., CD101 in salt or neutral form) in the bloodstream of a subject once the pharmaceutical composition is intravenously administered. In some embodiments, the intravenous precipitation of CD101 causes local irritations at the site of injection (e.g., pain or tenderness at the injection site, itching, bruising, and/or swelling of the skin, venous discoloration (e.g., darkening of the blood vein leading away from the site of injection), and skin rash). The intravenous solubility promoter in a pharmaceutical composition of the invention decreases the intravenous precipitation of CD101 in the bloodstream of a subject relative the intravenous precipitation of CD101 if it was in a composition without the intravenous solubility promoter. In some embodiments, a pharmaceutical composition that includes between 0.4 mg/mL and 10 mg/mL CD101 and an intravenous solubility promoter exhibits reduced local irritation upon intravenous administration to the subject.

The amount of an intravenous solubility promoter in a pharmaceutical composition may depend on, e.g., the concentration of CD101 in the pharmaceutical composition, and/or the pH of the pharmaceutical composition. In some embodiments, the weight to weight (w/w) ratio of the intravenous solubility promoter to the CD101 in the pharmaceutical composition is at least 2 (e.g., between 2 and 8, e.g., 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, or 8). Examples of intravenous solubility promoters that may be included in a pharmaceutical composition described herein include, but are not limited to, e.g., polysorbate 20 (Tween 20; polyoxyethylene (20) sorbitan monolaurate), polysorbate 40 (Tween40; polyoxyethylene (40) sorbitan monopalmitate), polysorbate 60 (Tween 60; polyoxyethylene (60) sorbitan monostearate), polysorbate 80 (Tween 80;

polyoxyethylene (80) sorbitan monooleate), β-cyclodextrin, polyoxyl 35 castor oil (Cremophor EL), polyoxyl 40 hydrogenated castor oil (Cremophor RH 40), polyoxyl 60 hydrogenated castor oil (Cremophor RH 60), D-α-tocopheryl polyethylene glycol 1000 succinate (TPGS), sorbitan monooleate (Span 20), polyoxyl 8 stearate (PEG 400 monosterate), polyoxyl 40 stearate (PEG 1750 monosterate), PEG 400 caprylic/capric glycerides (Labrasol), PEG 300 oleic glycerides (Labrafil M-1944CS), phosphatidylcholine (lecithin), alkylglucoside, sucrose monolaurate, sucrose monooleate, and polyoxyethylene-polyoxypropylene block copolymer (Poloxamer (e.g., poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, poloxamer 105 benzoate, and poloxamer 182 dibenzoate)). In some embodiments, the alkylglucoside is an alkyl monoglucoside (e.g., hexylglucoside, heptaglucoside, octylglucoside, nonaglucoside, decylglucoside, dodecylglucoside, or tetradecylglucoside). In some embodiments, the alkylglucoside is an alkyl diglucoside (e.g., hexylmaltoside, heptamaltoside, octylmaltoside, nonamaltoside, decylmaltoside, dodecylmaltoside (e.g., dodecyl-β-D-maltoside (DDM)), or tetradecylmaltoside (e.g., tetradecyl-β-D-maltoside (TDM))). In some embodiments, the intravenous solubility promoter in the pharmaceutical composition is polysorbate 80.

The concentration of CD101 in a pharmaceutical composition for intravenous administration described herein may be between 0.4 mg/mL and 4 mg/mL (e.g., 0.4, 0.5, 0.6, 0.7, 0.8, 0.9, 1, 1.1, 1.2, 1.3, 1.4, 1.5, 1.6, 1.7, 1.8, 1.9, or 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or 4 mg/mL). In some embodiments, the concentration of CD101 in a pharmaceutical composition for intravenous administration described herein is 0.8±0.2 mg/mL. In some embodiments, the concentration of CD101 in a pharmaceutical composition for intravenous administration described herein is 1.6±0.2 mg/mL.

A pharmaceutical composition for intravenous administration of the invention may also include a buffer. A buffer functions to maintain the pH of the composition. In some embodiments, a pharmaceutical composition for intravenous administration of the invention has a pH of between 5 and 7 (e.g., 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, or 7). A buffer included in a pharmaceutical composition for intravenous administration described herein may be, e.g., histidine, citrate, succinate, lactate, propanoate, arginine, tris(hydroxymethyl)aminomethane (tris), glycine, acetate, or formate.

Furthermore, a saccharide (e.g., mannitol, sucrose, trehalose, maltose, dextrose, or lactose) may also be included in a pharmaceutical composition of the invention. A pharmaceutical composition for intravenous injection including an aqueous solution including between 0.4 mg/mL and 10 mg/mL CD101 may include between 0.12% and 0.6% (w/w) of a saccharide (e.g., between 0.12% and 0.58% (w/w), between 0.12% and 0.56% (w/w), between 0.12% and 0.54% (w/w), between 0.12% and 0.52% (w/w), between 0.12% and 0.5% (w/w), between 0.12% and 0.48% (w/w), between 0.12% and 0.46% (w/w), between 0.12% and 0.44% (w/w), between 0.12% and 0.42% (w/w), between 0.12% and 0.4% (w/w), between 0.12% and 0.38% (w/w), between 0.12% and 0.36% (w/w), between 0.12% and 0.34% (w/w), between 0.12% and 0.32% (w/w), between 0.12% and 0.3% (w/w), between 0.12% and 0.28% (w/w), between 0.12% and 0.26% (w/w), between 0.12% and 0.24% (w/w), between 0.12% and 0.22% (w/w), between 0.12% and 0.2% (w/w), between 0.12% and 0.18% (w/w), between 0.12% and 0.16% (w/w), or between 0.12% and 0.14% (w/w) of a saccharide; about 0.12% (w/w), about 0.14% (w/w), about 0.16% (w/w), about 0.18% (w/w), about 0.2% (w/w), about 0.22% (w/w), about 0.24% (w/w), about 0.26% (w/w), about 0.28% (w/w), about 0.3% (w/w), about 0.32% (w/w), about 0.34% (w/w), about 0.36% (w/w), about 0.38% (w/w), about 0.4% (w/w), about 0.42% (w/w), about 0.44% (w/w), about 0.46% (w/w), about 0.48% (w/w), about 0.5% (w/w), about 0.52% (w/w), about 0.54% (w/w), about 0.56% (w/w), about 0.58% (w/w), or about 0.6% (w/w) of a saccharide). In some embodiments, the saccharide in the pharmaceutical composition is mannitol.

A pharmaceutical composition including an effective amount of CD101 (e.g., CD101 in salt or neutral form) and an intravenous solubility promoter in a lyophilized composition may include between 2% and 10% (w/w) of a saccharide (e.g., between 2% and 9% (w/w), between 2% and 8% (w/w), between 2% and 7% (w/w), between 2% and 6% (w/w), between 2% and 5% (w/w), between 2% and 4% (w/w), or between 2% and 3% (w/w) of a saccharide; about 2% (w/w), about 3% (w/w), about 4% (w/w), about 5% (w/w), about 6% (w/w), about 7% (w/w), about 8% (w/w), about 9% (w/w), or about 10% (w/w) of a saccharide).

A pharmaceutical composition of the invention may also include an effective amount of CD101 and an intravenous solubility promoter in a lyophilized composition. The lyophilized composition may include a weight to weight (w/w) ratio of the intravenous solubility promoter to the CD101 that is between 2 and 8 (e.g., 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, or 8). The CD101 in the lyophilized composition may be in its salt or neutral form. The lyophilized composition may be reconstituted to provide an aqueous solution having a pH of between 5 and 7 (e.g., 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, or 7).

Therapy

Methods of the invention include, e.g., methods of treating or preventing a fungal infection (e.g., a fungal infection caused by *Candida* spp. or *Aspergillus* spp.) in a subject by intravenously administering to the subject a pharmaceutical composition described herein. When using a pharmaceutical composition including CD101 (e.g., CD101 in salt or neutral form) and an intravenous solubility promoter in a lyophilized composition, the pharmaceutical composition may first be reconstituted to form an aqueous solution (e.g., an aqueous solution having a concentration of the CD101 that is between 0.4 mg/mL and 10 mg/mL), which can then be intravenously administered to the subject.

Methods of treating or preventing a fungal infection described herein exhibit reduced local irritation upon intravenous administration of a pharmaceutical composition of the invention to a subject. The subject may experience reduced local irritation or no local irritation, e.g., pain or tenderness at the injection site, itching, bruising, and/or swelling of the skin, venous discoloration (e.g., darkening of the blood vein leading away from the site of injection), and skin rash, upon intravenous administration of a pharmaceutical composition of the invention, relative to the irritation experienced when intravenously administered other compositions.

In some embodiments of the methods of the invention, a pharmaceutical composition described herein may be intravenously administered to the subject by infusion. The intravenous infusion may be performed at a constant infusion rate of between 2 mL/minute and 9 mL/minute (e.g., 2, 2.5, 3, 3.5, 4, 4.5, 5, 5.5, 6, 6.5, 7, 7.5, 8, 8.5, or 9 mL/minute).

In some embodiments, the pharmaceutical composition may be administered to the subject over 30 to 120 minutes (e.g., 30, 40, 50, 60, 70, 80, 90, 100, 110, or 120 minutes). In certain embodiments of the methods of the invention, 100 mL to 500 mL (e.g., 100, 105, 110, 115, 120, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, or 500 mL; 100 mL to 480 mL, 100 mL to 460 mL, 100 mL to 440 mL, 100 mL to 420 mL, 100 mL to 400 mL, 100 mL to 380 mL, 100 mL to 360 mL, 100 mL to 340 mL, 100 mL to 320 mL, 100 mL to 300 mL, 100 mL to 280 mL, 100 mL to 260 mL, 100 mL to 240 mL, 100 mL to 220 mL, 100 mL to 200 mL, 100 mL to 190 mL, 100 mL to 180 mL, 100 mL to 170 mL, 100 mL to 160 mL, 100 mL to 150 mL, 100 mL to 140 mL, or 100 mL to 130 mL; 120 mL to 500 mL, 140 mL to 500 mL, 160 mL to 500 mL, 180 mL to 500 mL, 200 mL to 500 mL, 220 mL to 500 mL, 240 mL to 500 mL, 260 mL to 500 mL, 280 mL to 500 mL, 300 mL to 500 mL, 320 mL to 500 mL, 340 mL to 500 mL, 360 mL to 500 mL, 380 mL to 500 mL, 400 mL to 500 mL, 420 mL to 500 mL, 440 mL to 500 mL, 460 mL to 500 mL, or 480 mL to 500 mL) of a pharmaceutical composition (e.g., a pharmaceutical composition having a concentration of CD101 at 0.4 mg/mL, 0.8 mg/mL, or 1.6 mg/mL) is administered to the subject in 20 minutes to 60 minutes (e.g., 20, 25, 30, 35, 40, 45, 50, 55, or 60 minutes). In some embodiments, 100 mL to 250 mL (e.g., 105, 115, 125, 135, 145, 155, 165, 175, 185, 195, 205, 215, 225, 235, 245, or 250 mL) of a pharmaceutical composition (e.g., a pharmaceutical composition having a concentration of CD101 at 0.4 mg/mL, 0.8 mg/mL, or 1.6 mg/mL) is administered to the subject in 30 minutes. In some embodiments, 125 mL to 250 mL (e.g., 125, 135, 145, 155, 165, 175, 185, 195, 205, 215, 225, 235, 245, or 250 mL) of a pharmaceutical composition (e.g., a pharmaceutical composition having a concentration of CD101 at 0.4 mg/mL, 0.8 mg/mL, or 1.6 mg/mL) is administered to the subject in 60 minutes. In some embodiments, 250 mL of a pharmaceutical composition (e.g., a pharmaceutical composition having a concentration of CD101 at 0.4 mg/mL, or 0.8 mg/mL, or 1.6 mg/mL) is administered to the subject in 30 minutes. In some embodiments, 250 mL of a pharmaceutical composition (e.g., a pharmaceutical composition having a concentration of CD101 at 0.4 mg/mL, 0.8 mg/mL, or 1.6 mg/mL) is administered to the subject in 60 minutes.

Furthermore, in some embodiments, at least one dose (e.g., a dose between 50 mg and 800 mg of CD101; about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 mg of CD101) may be intravenously administered to the subject every 5 to 15 days (e.g., every 5, 6, 7, 8, 9, 10, 11, 12, 13, 14, or 15 days). In some embodiments, one dose (e.g., a dose between 50 mg and 800 mg of CD101; about 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, or 800 mg of CD101) may be intravenously administered to the subject every 5 to 15 days (e.g., every 5, 6, 7, 8, 9, 10, 11, 12, 13, 14, or 15 days).

In some embodiments of the methods of the invention, the subject may be immunocompromised, and thus, is at a higher risk for developing a fungal infection. In some embodiments, the subject is being prepared for an invasive medical procedure or undergoing long term antibiotic therapy. In some embodiments, the subject has been diagnosed with humoral immune deficiency, T cell deficiency, neutropenia, asplenia, or complement deficiency. In some embodiments, the subject is being treated or is about to be treated with immunosuppresive drugs. In some embodiments, the subject has been diagnosed with a disease which causes immunosuppression (e.g., cancer or acquired immunodeficiency syndrome). In some embodiments, the subject has cancer (e.g., leukemia, lymphoma, or multiple myeloma). In some embodiments, the subject has undergone or is about to undergo immunosuppression therapy. In some embodiments, the subject has undergone or is about to undergo hematopoietic stem cell transplantation. In some embodiments, the subject has undergone or is about to undergo an organ transplant. In some embodiments, subjects may receive prophylaxis treatment while being prepared for an invasive medical procedure (e.g., preparing for surgery, such as receiving a transplant, stem cell therapy, a graft, a prosthesis, receiving long-term or frequent intravenous catheterization, or receiving treatment in an intensive care unit).

In some embodiments of the methods described herein, the fungal infection to be treated or prevented is selected from candidemia, invasive candidiasis, *Tinea capitis, Tinea corporis, Tinea pedis*, onychomycosis, perionychomycosis, *Pityriasis versicolor*, oral thrush, vaginal candidiasis, respiratory tract candidiasis, biliary candidiasis, eosophageal candidiasis, urinary tract candidiasis, systemic candidiasis, mucocutaneous candidiasis, aspergillosis, mucormycosis, paracoccidioidomycosis, North American blastomycosis, histoplasmosis, coccidioidomycosis, sporotrichosis, fungal sinusitis, or chronic sinusitis.

In some embodiments of the methods described herein, the fungal infection is candidemia or invasive candidiasis.

In some embodiments of the methods described herein, the fungal infection to be treated or prevented is an infection of *Candida albicans, C. glabrata, C. dubliniensis, C. krusei, C. parapsilosis, C. tropicalis, C. orthopsilosis, C. guilliermondii, C. rugosa, C. auris, C. lusitaniae, Aspergillus fumigatus, A. flavus, A. terreus, A. niger, A. candidus, A. clavatus*, or *A. ochraceus*. The following examples are put forth so as to provide those of ordinary skill in the art with a complete disclosure and description of how the methods and compositions claimed herein are performed, made, and evaluated, and are intended to be purely exemplary of the disclosure and are not intended to be limiting.

EXAMPLES

Example 1: Solubility of CD101 in Various Media

Table 1 below provides the solubility of CD101 acetate in different solutions.

TABLE 1

| Medium | Solubility (mg/mL) |
|---|---|
| 5% Dextrose Solution (USP) | >12* |
| 5% D-Mannitol | >4 * |
| Lactated Ringer's Solution for Injection (USP) [1] | <0.1 |

TABLE 1-continued

| Medium | Solubility (mg/mL) |
|---|---|
| Lactated Ringer's Solution for Injection (USP) [1] (Prepared from Stock in USP Water with 0.7% Tween 20 (polysorbate 20)) | >0.8* |
| 0.9% Saline (USP) [1] | <0.18 |
| 0.9% Saline (USP) with 1% Tween 20 [1] | >2.6* |
| 0.9% Saline (USP) with 2.5% Tween 80 (polysorbate 80) | >3.5 |
| 0.9% Saline (USP) with 0.5% Tween 80 | >3.5 |
| 0.9% Saline (USP) with 0.125% Tween 80 | >0.8 |
| 0.45% Saline (USP) [1] | >1.3* |
| 0.225% Saline (USP) [1] | >1.2* |
| 0.09% Saline | >1.4* |
| Phosphate buffered saline (PBS buffer), pH 7.4 | 0.005-0.007 (5-7 µg/mL) |
| 1:10 diluted PBS buffer, pH 7.4 | >2.1* |
| PBS buffer with 1% Tween 20, pH 7.4 | >0.37* |
| PBS buffer with 2.5% Tween 80, pH 7.4 | >4 |
| 0.85% Tween 80 in PBS buffer, pH 7.4 | >4.1* |
| 50-100 mM Acetate buffer, pH 4.5 | >45* |
| 50 mM Acetate buffer pH 4.5 with 0.4% Tween 20 | >31.3* |
| 2.5% Tween 80, 5% mannitol, 0.3% acetic acid, pH 4.5 | >16* |
| 0.3% acetic acid, 5% mannitol, 2.5% Tween 80, pH 4.5 | >15* |
| KCl (150 mM) | <0.2 |
| Water (USP) | >100* |
| Potassium chloride (150 mM) | 0.16 |
| Potassium chloride (15 mM) | >1.7 |
| 100 mM Phosphate buffer, pH 7.4 | 0.007-0.010 (7-10 µg/mL) |
| 100 mM Tris buffer, pH 7.4 | >52* |
| Lactate buffer (100 mM), pH 7.4 | >51* |
| Lactate buffer (100 mM), pH 6.5 | >48* |
| 5% Citric Acid | >18.6* |
| 0.9% Saline Solution (USP), 4% dodecylmaltoside (DDM), 1% Tween 20 | >10* |
| 0.9% Saline Solution (USP), 7% tetradecylmaltoside (TDM) | >11* |

*Maximum solubility was not reached
[1] IV injection solution

CD101 acetate is soluble (>1 mg/mL) in 5% dextrose, 5% mannitol and 0.22%-0.45% Sterile Saline Solution, but demonstrated a significant decrease in solubility at higher salt concentrations such as normal saline (0.9% Sterile Saline Solution) or Lactated Ringer's Solution and is nearly insoluble in PBS buffer. The addition of a non-ionic surfactant such as polysorbate 20 (Tween 20) and polysorbate 80 (Tween 80) improves the solubility of CD101 acetate in high salt solutions such as 0.9% Sterile Saline, neutral pH phosphate buffer media, and also in Lactated Ringer's solution.

Example 2: Investigation of Use of Tween 80 for Use in CD101 Acetate Formulations Methods CD101 acetate 20 mg/kg dose was prepared in w/w in 5% dextrose solution (CD101 acetate at 4 mg/mL solution) for the following solutions using the salt to free base correction factor of 0.8784 for CD101 acetate:

CD101 Acetate Control:

No Tween 80 used. The pH of the solution is 5.14 (22.7 mg CD101 acetate into 5 mL 5% Dextrose)

CD101 Acetate 0.5% Tween 80:

0.5% w/w Tween 80 used. The pH of the solution is 5.21 (22.8 mg CD101 acetate into 5 mL 5% Dextrose with 0.5% w/w Tween 80 (0.1 g Tween 80+19.9 g 5% Dextrose))

CD101 Acetate 1.0% Tween 80:

1.0% w/w Tween 80 used. The pH of the solutions is 5.27 (22.9 mg CD101 acetate into 5 mL 5% Dextrose with 1.0% w/w Tween 80 (0.2 g Tween 80+19.8 g 5% Dextrose))

CD101 Acetate 2.5% Tween 80:

2.5% w/w Tween 80 used. The pH of the solutions is 5.29 (22.7 mg CD101 acetate into 5 mL 5% Dextrose with 2.5% w/w Tween 80 (0.5 g Tween 80+19.5 mL 5% Dextrose))

CD101 Acetate 1.0% Tween 80, pH Adjusted to 6.64:

1.0% w/w Tween 80 used. The pH of the solution was adjusted to 6.64 using 0.1 N NaOH. (22.9 mg CD101 acetate into 5 mL 5% Dextrose with 1.0% w/w Tween 80 (0.2 g Tween 80+19.8 g 5% Dextrose))

1.5 mL each of CD101 acetate 20 mg/kg dose (CD101 acetate at 4 mg/mL solution) prepared above was added via syringe drop wise to the following solutions and were observed for drug insolubility in the solution (A) 5 mL 0.9% saline solution, or (B) 5 mL PBS buffer.

Results

CD101 acetate prepared in 1.0% Tween 80 w/w in 5% dextrose solution (CD101 acetate at 4 mg/mL), pH 5.4 solution and added to (A) 5 mL 0.9% saline solution and (B) 5 mL PBS buffer: both (A) and (B) were clear after CD101 acetate addition. CD101 acetate prepared in 1.0% Tween 80 w/w in 5% dextrose solution (CD101 acetate at 4 mg/mL), adjusted to pH 6.64 using 0.1 N NaOH solution and added to (A) 5 mL 0.9% saline solution and (B) 5 mL PBS buffer: both (A) and (B) were clear after CD101 acetate addition. The results are summarized in Table 2 below.

TABLE 2

| | Control | 0.5% | 1.00% | 2.5% | 1% (pH 6.64) |
|---|---|---|---|---|---|
| | CD101 acetate in 5% dextrose without Tween 80 | CD101 acetate in 5% dextrose and 0.5% Tween 80 | CD101 acetate in 5% dextrose and 1.0% Tween 80 | CD101 acetate in 5% dextrose and 2.5% Tween 80 | CD101 acetate in 5% dextrose and 1.0% Tween 80, adjusted to 6.64 pH using 0.1N NaOH |
| PH | 5.3 | 5.4 | 5.3 | 5.3 | 6.64 |
| 1.5 mL added to (A) 5 mL 0.9% saline solution | Precipitation; cloudy | clear | Clear | Clear | Clear |
| 1.5 mL added to (B) 5 mL PBS buffer | Precipitation; cloudy | Precipitation; cloudy | Clear | Clear | Clear at 5 minutes; became clear overnight |

Example 3: PBS Buffer Drop Test

Different concentrations of CD101 acetate were prepared in the various vehicles listed in Tables 2-5. These solutions were tested for solubility in the PBS drop test, which involved adding the solution dropwise into PBS solution (1:4.3 dilution) and visually observing the resulting solution for any precipitation. PBS buffer serves as a surrogate for plasma, and the PBS drop test is used to evaluate the potential for insolubility as the drug enters the bloodstream at the injection site.

Table 3 below provides the solubility observations of CD101 acetate in different IV infusion solutions in the presence and absence of Tween 80 in a PBS drop test.

TABLE 3

| Vehicle | pH | Tween 80 | CD101 concentration | Appearance upon PBS drop test |
|---|---|---|---|---|
| 0.9% Saline | pH 5.3 | 0.0% | 4 mg/mL | Not Soluble (Cloudy Precipitate) |
|  | pH 5.3 | 1.0% | 4 mg/mL | Not Soluble (Cloudy Precipitate) |
|  | pH 7.2 | 1.75% | 4 mg/mL | Clear |
|  | Reverse Addition* | 1.75% | 4 mg/mL | Clear |
|  | pH 5.3 | 2.8% | 4 mg/mL | Clear |
|  | pH 6.6 | 2.5% | 4 mg/mL | Clear |
|  | pH 7.2 | 2.5% | 4 mg/mL | Clear |
| PBS buffer pH 7.4 | pH 7.13 | 1.75% | 4 mg/mL | Clear |
| 5% Mannitol/ 30 mM Na Lactate | pH 5.45 | 2.5% | 4 mg/mL | Clear |
| 5% Mannitol/ 0.3% Acetic Acid | pH 3.54 | 2.5% | 4 mg/mL | Clear |
| 5% Mannitol/ 25 mM Na Acetate | pH 4.63 | 2.5% | 4 mg/mL | Clear |

*First CD101 acetate and Tween 80 were mixed together and then 0.9% saline solution was added.

Table 4 below provides the solubility observations of CD101 acetate in different 5% Dextrose IV infusion solutions in a PBS drop test.

TABLE 4

| Vehicle | CD101 concentration pH, and appearance in vehicle | CD101 concentration and pH upon PBS drop test | Appearance upon PBS drop test |
|---|---|---|---|
| 1.75% Tween 80 and 5% Dextrose, pH 5.0 | 4.0 mg/mL; pH 5.0 (unadjusted); Clear solution | 0.92 mg/mL in PBS; pH = 5.35 | Slightly cloudy (micro particulate suspension) after standing over 1 hr |
| 1.0% Tween 80 and 5% Dextrose, pH 5.0 | 4.0 mg/mL; pH 5.0 (unadjusted) Clear solution | 0.92 mg/mL in PBS; pH = 7.1 | Cloudy after standing over 1 hr |
| 0.0% Tween 80, 5% Dextrose, pH 5.0 | 4.0 mg/mL; pH 5.0 (unadjusted) Clear solution | 0.92 mg/mL in PBS; pH = 7.1 | Immediately cloudy suspension |
| 0.0% Tween 80, 5% Dextrose, pH 7.0 | 4.0 mg/mL; pH 7.0 (adjusted) Clear solution | 0.92 mg/mL in PBS; pH = 7.4 | Immediately cloudy suspension |

Table 5 below provides the solubility observations of CD101 acetate in different 5% Mannitol IV infusion solutions in a PBS drop test.

TABLE 5

| Vehicle | CD101 concentration, pH, and appearance in vehicle | CD101 concentration and pH upon PBS drop test | Appearance upon PBS drop test |
|---|---|---|---|
| 0.3% acetic acid, 2.5% Tween 80 and 5% mannitol, pH 4.5 | 4 mg/mL; Clear solution; pH = 4.51 | 0.92 mg/mL in PBS; pH = 6.0 | Clear |
| 0.3% acetic acid, 2.5% Tween 80 and 5% mannitol, pH 4.5 | 6.0 mg/mL; Clear solution; pH = 4.49 | 1.4 mg/mL in PBS; pH = 5.4 | Clear |
| 0.3% acetic acid, 1.25% Tween 80 and 5% mannitol, pH 4.5 | 6.0 mg/mL; Clear solution; pH = 4.5 | 1.4 mg/mL in PBS | Clear |
| 0.3% acetic acid, 2.5% Tween 80 and 5% mannitol, pH 4.5 | 8.0 mg/mL; Clear solution; pH = 4.50 (adjusted) | 1.8 mg/mL in PBS; pH = 5.5 | Clear |
| 0.3% acetic acid, 2.5% Tween 80 and 5% mannitol, pH 4.5 | 16 mg/mL; Clear solution; pH = 4.50 (adjusted) | 3.7 mg/mL in PBS; pH = 5.5 | Clear (slight cloudiness upon addition and turned clear after) |

Table 6 below provides the solubility observations of CD101 at concentrations of 2 and 3 mg/mL in 0.76% mannitol human IV infusion solutions containing 0.50% Tween 80 in a PBS drop test.

TABLE 6

| Vehicle | CD101 concentration and appearance in vehicle | CD101 concentration upon PBS drop test | Appearance upon PBS drop test |
|---|---|---|---|
| 0.50% Tween 80, 0.76% mannitol, 0.125% sodium lactate in 3.5% dextrose solution, pH ~5.5 | 2 mg/mL; Clear solution | 0.47 mg/mL in PBS, | Clear |
| 0.50% Tween 80, 0.76% mannitol, 0.125% sodium lactate in 3.5% dextrose solution, pH ~5.5 | 3 mg/mL; Clear solution | 0.70 mg/mL in PBS, | Cloudy after 30 mins |

Conclusion

The solubility studies of CD101 intravenous (IV) formulations when introduced into PBS buffer solutions demonstrated that higher Tween 80 concentrations facilitated better solubility. A 6 mg/mL CD101 solution formulated in 1.25% Tween 80, 5% mannitol, 0.3% glacial acetic acid, pH ~4.5 vehicle remained soluble in PBS for at least 1 hour at room temperature. The data indicate that a Tween 80 concentration greater than 1% w/w or w/v is required to avoid insolubility of CD101 in PBS buffer, which is a surrogate for plasma. Precipitation of CD101 at the site of injection may result in irritation in the tissue at the injection site and the vein leading away from the injection site.

Example 4: Solubility of CD101 in Intravenous (IV) Formulations

Solubility of CD101-containing formulations with different percentages of Tween 80 (also referred to as polysorbate 80) was evaluated in a "PBS drop test." This involved preparing a known concentration of CD101 in a formulation and injecting the formulation into PBS to visually examine for precipitation. This test was used to assess if a CD101-containing formulation would remain soluble in blood during IV infusions.

Vehicle Formulations Tested (1) 1.25% Tween 80, 5% mannitol, 0.3% glacial acetic acid, pH ~4.5

(2) 0.50% Tween 80, 0.76% mannitol, 0.125% sodium lactate in 3.5% dextrose solution, pH ~5.5

Different concentrations of CD101 acetate were prepared in vehicles (1) and (2) and tested for solubility in the PBS drop test.

Dilution into PBS Buffer Reservoir (PBS Drop Test)

Add dropwise the formulated solution into PBS solution (1:4 dilution). Visually observe the resulting solution upon addition for any precipitation.

Results 1.25% Tween 80, 5% Mannitol, 0.3% Glacial Acetic Acid, pH ~4.5

One mL of a 6 mg/mL CD101 acetate solution was prepared in the formulation (1.25% Tween 80, 5% mannitol, 0.3% glacial acetic acid, pH ~4.5). Following formulation, 0.25 mL of the formulated solution was introduced into 1 mL of the PBS solution (PBS drop test). The PBS drop test demonstrated that the formulated 6 mg/mL solution remained soluble in PBS for at least 1 hour. This test was repeated to confirm the observation.

0.50% Tween 80, 0.76% Mannitol, 0.125% Sodium Lactate in 3.5% Dextrose Solution, pH ~5.5

One mL of a 2 mg/mL CD101 acetate solution was prepared in the formulation (0.50% Tween 80, 0.76% mannitol, 0.125% sodium lactate in 3.5% dextrose solution, pH ~5.5. Following formulation, 0.25 mL of the formulated solution was introduced into 1 mL of the PBS solution (PBS drop test). The PBS drop test demonstrated that the formulated 2 mg/mL solution remained soluble in PBS for at least 1 hour. This test was repeated to confirm the observation.

One mL of a 3 mg/mL CD101 solution was prepared in the same formulation (0.50% Tween 80, 0.76% mannitol, 0.125% sodium lactate in 3.5% dextrose solution, pH ~5.5). Following formulation, 0.25 mL of the formulated solution was introduced into 1 mL of the PBS solution (PBS drop test). The PBS drop test indicated that the formulated 3 mg/mL solution remained soluble in PBS for 15 to 30 minutes. This test was repeated to confirm the observation.

Conclusion

The solubility of CD101 IV formulations when introduced into phosphate-buffered saline (PBS) indicated that higher Tween 80 concentrations facilitated better solubility. A 6 mg/mL CD101 acetate solution formulated in 1.25% Tween 80, 5% mannitol, 0.3% glacial acetic acid, pH ~4.5 vehicle remained soluble in PBS for at least 1 hour. A lower concentration (2 mg/mL) CD101 solution formulated in 0.50% Tween 80, 0.76% mannitol, 0.125% sodium lactate in 3.5% dextrose solution, pH ~5.5 remained soluble in PBS for at least 1 hour. In contrast, a 3 mg/mL CD101 solution prepared in the 0.50% Tween 80, 0.76% mannitol, 0.125% sodium lactate in 3.5% dextrose solution, pH ~5.5 was soluble in PBS for only 15 to 30 minutes.

Example 5: 14-Day Repeat-Dose Intravenous Infusion Toxicity Study with CD101 Acetate in Sprague Dawley Rats The primary purpose of this study was to evaluate the toxicity of CD101 when administered intravenously as a 20-minute infusion into the lateral tail vein of Sprague Dawley rats for fourteen consecutive days. A positive control group (Eraxis®) with a similar structure and pharmacodynamic activity was included in the study design.

Methods

The test article, CD101 acetate, was a white to off-white powder. The test article was prepared into dosing formulations for intravenous dose administration. One hundred experimentally naïve Sprague Dawley rats (50 males and 50 females), a minimum of 8 weeks old and weighing 255-318 grams (males) and 192-215 (females) at the outset of the study were assigned to treatment groups as shown in Table 7 below:

TABLE 7

| Group | Dose Level ®* (mg/kg/day) | Concentration ® (mg/mL) | Dose Volume (mL/kg) | Number of Animals | |
|---|---|---|---|---|---|
| | | | | Male | Female |
| 1. Vehicle control | 0 | 0 | 5.0 | 10 | 10 |
| 2. Positive Control (Eraxis ®)# | 40 | 8 | 5.0 | 10 | 10 |
| 3. CD101 acetate low-dose | 2 | 0.4 | 5.0 | 10 | 10 |
| 4. CD101 acetate mid-dose | 6 | 1.2 | 5.0 | 10 | 10 |
| 5. CD101 acetate high-dose | 20 | 4.0 | 5.0 | 10 | 10 |

@ The total volume administered over a 20-minute continuous infusion was less than the maximum allowable volume of 1 mL/min in the rat species
*These dose levels represent the salt free (base) form of the test article
Each Eraxis ® vial contained 100 mg of Anidulafungin in lyophilized form All animals were dosed on Days 1 through 3 inclusive. As a result of tail vein irritation observed among all study groups, dose administration was suspended on Day 4 to allow the tails to recover. Dosing resumed on Day 5 and continued for a maximum of ten additional days (Days 5 through 14 inclusive). Animals that could no longer be dosed during this time remained on study.

Results and Conclusion

Male and female Sprague Dawley rats were to receive CD101 acetate at doses of 0, 2, 6 and 20 mg/kg/day (Groups 1, 3, 4 and 5, respectively) or Eraxis® (the positive control article, Group 2) at a dose of 40 mg/kg/day, intravenously as a 20 minute infusion into the left or right lateral tail vein for fourteen consecutive days. During the first three treatment days, all animals were dosed with the first vehicle used on this study (1.75% Tween 80/5% Dextrose: Groups 1 and 3-5; 5% Dextrose: Group 2). As a result of the localized tail swelling observed during the first three days of treatment, study Day 4 served as a drug-free day to alleviate tail vein irritation. Dose administration resumed on Day 5 using a new vehicle (5% Mannitol/2.5% Tween 80/0.3% acetic acid: Groups 1 and 3-5; 5% Mannitol/0.3% acetic acid: Group 2) for the remainder of the treatment period (Days 5-14). Those animals that could no longer be dosed because of severe vein irritation were retained on study, untreated, until the end of the study (Day 15).

All animals were dosed on Days 1-3. Beginning on Day 5, some of the animals could no longer be dosed as a result of tail swelling/lesions. Ten percent (10%) of vehicle control males, thirty percent (30%) of Positive Control (Group 2) males and 30% of high dose males (Group 5) were dosed for less than the intended ten-day duration with the second vehicle control used on Days 5-14. Ten percent (10%) of females treated with the low dose (Group 3), 10% with the mid-dose (Group 4), and 90% with the high dose (Group 5) did not receive ten consecutive days of treatment with the second vehicle from Days 5-14.

Clinical signs indicative of tail vein irritation were recorded for all animals on this study (Groups 1-5) and included a combination of the following: a red or purple discolored tail, the presence of white and/or yellow patches on the tail, a swollen tail, and abrasions or scabs. The incidence of tail vein irritation when using the first vehicle during Days 1-3 (1.75% Tween 80 and 5% Dextrose: Groups 1 and 3-5; 5% Dextrose: Group 2) was highest for males and females treated with Eraxis® and CD101 acetate at doses of 6 and 20 mg/kg/day. Distinctions between dose groups when using the second vehicle during Days 5-14 (5% Mannitol, 2.5% Tween 80, and 0.3% Acetic Acid: Groups 1 and 3-5); 5% Mannitol and 0.3% Acetic Acid: Group 2) were not as evident as when using the first vehicle. The vein irritation observed during Days 5-14 was only marginally higher for Group 2 (Eraxis®) and Group 5 (CD101 acetate at 20 mg/kg/day) compared to the vein irritation for Group 1 and test article-treated Groups 3 and 4 during Days 5-14.

Example 6: A Single-Dose Intravenous Infusion Tolerability Study of CD101 in Cynomolgus Monkeys The objective of this study was to evaluate and compare the tolerability of CD101 when administered once by either a 20-minute or 60-minute intravenous infusion to cynomolgus monkeys. In addition, a vehicle similar to the intended initial clinical formulation was assessed when administered once by 20-minute intravenous infusion up to the highest feasible dose (10 mg/kg).

Methods

This study was divided into 2 phases (Table 8). In phase 1, CD101 acetate was administered in vehicle-1 (1.25% Tween 80, 5% mannitol, 0.3% glacial acetic acid adjusted to pH 4.5±0.1) as a single 20-minute (±2 minutes) intravenous infusion to 1 animal/sex/group at 0 and 30 mg/kg (Groups 1 and 2, respectively). In addition, CD101 acetate was administered in vehicle-1 as a single 60-minute (±5 minutes) intravenous infusion to 1 animal/sex/group at 0 and 30 mg/kg (Groups 3 and 4, respectively).

In phase 2, CD101 acetate was administered in vehicle-2 (0.50% Tween 80, 0.76% mannitol, 0.125% sodium lactate in 3.5% dextrose solution, pH 5.5±0.1) as a single 20-minute (±2 minutes) intravenous infusion to 1 animal/sex at 10 mg/kg (Group 5). Dosing was staggered so that Group 5 was dosed 2 days after Groups 1-4.

TABLE 8

| Group | Treatment | Dose Level (mg/kg) | Concentration [a] (mg/mL) | Dose Volume[b] (mL/kg) | # of Animals | |
|---|---|---|---|---|---|---|
| | | | | | Male | Female |
| 1 | Vehicle-1 | 0 | 0 | 5 | 1 | 1 |
| 2 | CD101 acetate in Vehicle-1 | 30 | 6 | 5 | 1 | 1 |
| 3 | Vehicle-1 | 0 | 0 | 5 | 1 | 1 |
| 4 | CD101 acetate in Vehicle-1 | 30 | 6 | 5 | 1 | 1 |
| 5 | CD101 acetate Vehicle-2 | 10 | 2 | 5 | 1 | 1 |

[a] = The test article formulations were corrected for purity/potency using a correction factor of 1.183.
[b] = Dose volume delivered by infusion over a 20-minute (±2 minutes) period for Groups 1, 2, and 5 and over a 60-minute (±5 minutes) period for Groups 3 and 4.

Results No other remarkable clinical observations were observed and there were no differences that could be attributed to the duration of infusion (i.e., 20 minutes versus 60 minutes).

Conclusion

The results of this study indicate no differences between the tolerability of a 20-minute and 60-minute infusion. In addition, use of a vehicle can be administered safely to cynomolgus monkeys up to the highest feasible dose (10 mg/kg) in the vehicle.

Example 7. Efficacy CD101 in the Treatment of Candida auris Infection in a Murine Model of Disseminated Candidiasis Methods Female 6-8 week old CD-1 mice were immunosuppressed with cyclophosphamide (200 mg/kg) 3 days prior to infection and 150 mg/kg 1 day post-infection. On the day of infection, mice were inoculated with $3\times10^7$ C. auris blastospores via the lateral tail vein. Mice were randomized into 5 groups (n=5 for colony forming units (CFU) and n=10 for survival): CD101 20 mg/kg administered by intraperitoneal (IP) injection, fluconazole 20 mg/kg administered per os (PO), amphotericin B 0.3 mg/kg IP, and a vehicle control. Treatments were administered 2 hours post-infection (day 1) and again on day 4 of the study for a total of 2 doses. Mice were monitored daily and a survival curve was generated. CFU groups were sacrificed on day 8 of the study. One kidney was removed from each mouse, homogenized, plated on potato dextrose agar (PDA), and incubated at 35° C. for 2 days to determine CFU. The remaining survival mice were monitored until the end of the study (day 14).

Results

CD101 showed an average 3 log reduction in kidney CFU compared to fluconazole, amphotericin B, and vehicle treated groups, which was statistically significant (P=0.03, 0.03, and 0.04, respectively). At the end of the study, percent survival of mice in CD101, fluconazole, amphotericin B, vehicle, and untreated groups was 80, 0, 30, 20, and 0%, respectively (FIG. 1).

Conclusion

Taken together, our findings show that CD101 possesses potent antifungal activity against C. auris infection in a disseminated model of candidiasis. Additionally, treatment with CD101 resulted in a significantly higher overall percent survival.

Example 8. Evaluate the Ability of CD101 to Prevent and Treat Candida albicans Biofilms and Explore its Temporal Effect by Time Lapse Photography In this study, we determined the effect of CD101 on prevention and treatment of biofilms formed by Candida albicans in vitro, and evaluated the effect of CD101 (at effective concentration) on formation of biofilm in real time using Time Lapse Microscopy (TLM).

Materials and Methods

Test Compounds

CD101 powder stocks were reconstituted in water or Yeast Nitrogen Base (YNB) medium, and diluted in YNB to a final working concentration of 0.25 µg/ml and 1 µg/ml. YNB with no CD101 was prepared in parallel and used as controls. Fluconazole was used as a comparator.

Test Media

YNB and Sabouraud dextrose agar (SDA) media

CD101 (powder and reconstituted solution) stored at −80° C. when not in use.

Strains

C. albicans SC-5314 was used for the current study.

Activity of CD101 Against Candida Biofilms

In this study, biofilms were grown in vitro using a biofilm model (Chandra et al., Nature Protocols 3:1909, 2008) and the effect of CD101 on adhesion phase biofilms (representing prevention of biofilms) or mature phase biofilms (representing treatment of biofilms) was determined.

Activity Against Adhesion Phase (Prevention) or Mature Phase (Treatment) Biofilms Biofilms were formed on silicone elastomer (SE) discs using a catheter-associated-biofilm model (Chandra et al., Nature Protocols 3:1909, 2008; Chandra et al., J. Bacteriol. 183: 5385, 2001; Chandra et al., J. Dental Research 80: 903, 2001). For evaluation of activity against adhesion phase biofilms (prevention), Candida cells were adhered to catheter discs for 90 min. Next, discs were incubated for 24 h with CD101 (0.25 or 1 µg/ml concentrations) to allow biofilm formation. For evaluation of activity against mature phase biofilms (treatment), Candida cells were adhered to catheter discs for 90 min, then transferred to fresh media and incubated for a further 24 h to allow formation of biofilms. Mature biofilms were then exposed to CD101 (0.25 or 1 µg/ml concentrations) for another 24 h. Discs incubated with fluconazole or media alone were used as controls in all experiments.

At the end of drug exposure in both adhesion and mature phase biofilms, biofilms were quantified by measuring their metabolic activity using XTT assay (Chandra et al., Nature Protocols 3:1909, 2008; Chandra et al., J. Bacteriol. 183: 5385, 2001; Chandra et al., J. Dental Research 80: 903, 2001). Following incubation with drugs, discs were transferred to fresh plates containing phosphate buffered saline with XTT and menadione, incubated for 3 h at 37° C. and optical density was read at 492 nm. Separate batches of biofilms were stained with fluorescent dyes (FUN1™, CONA) and observed under Confocal Scanning Laser Microscope (CSLM) to evaluate biofilm architecture and thickness (Chandra et al., Nature Protocols 3:1909, 2008; Chandra et al., J. Bacteriol. 183: 5385, 2001).

Time Lapse Microscopy

The effective CD101 concentration obtained from the above experiments was used to monitor its effect on biofilm formation in real time using TLM, which involves capturing real-time images of a single frame at specific time intervals, allowing temporal monitoring of the interactions occurring between the drug and Candida biofilms. Captured images were combined in a time sequence, resulting in an animation depicting the sequence of events that occurred with the passage of time. Briefly, the discs with C. albicans (adhered for 90 min as above) were placed in a 35-mm-diameter glass-bottom Petri dish (MatTek Corp., Ashland, MA). Next, CD101 (dissolved in the growth medium) was added to the Petri dish, and incubated at 37° C. to allow formation of biofilm. Phase contrast images for this interaction were captured immediately from 0 h and followed up to 16-17 h on a Leica DMI 6000 B inverted microscope connected to a Retiga EXi Aqua camera (Q-imaging Vancouver British Columbia). To determine the structural changes in the maturing biofilm, both acquisition and analysis of a series of horizontal (xy) optical sections of the biofilm was done using Metamorph Imaging software (Molecular Devices, Downington, PA). Disc incubated with media alone was used as control.

Statistical Analyses

Statistical analyses for all data were performed using GraphPad Prism 6 software. Drug treated groups were compared to control untreated groups using unpaired t-tests. P-value of <0.05 was considered significant.

Results

Activity Against Adhesion Phase Biofilms (Prevention)

Figure 2B:
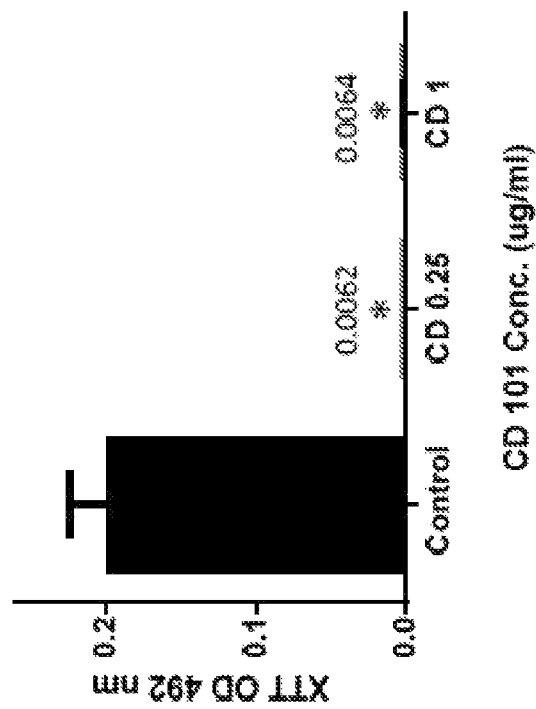
Figure 3F:
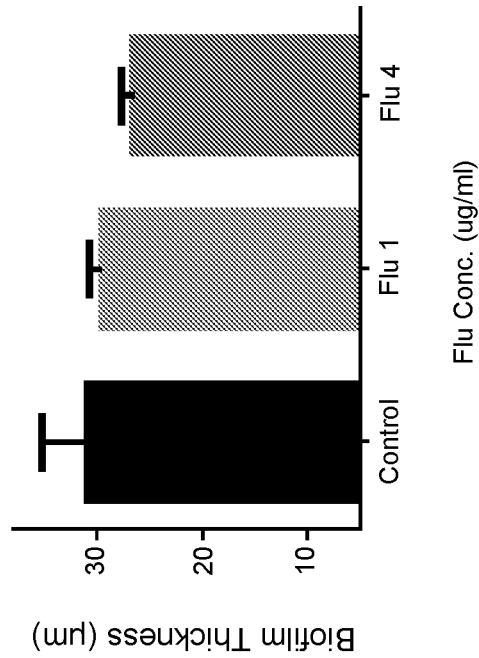
FIGS. 3F and 3G are bar graphs showing the thickness of *C. albicans* biofilms exposed to CD101 (FIG. 3F) and fluconazole (FIG. 3G).
Figure 3G:
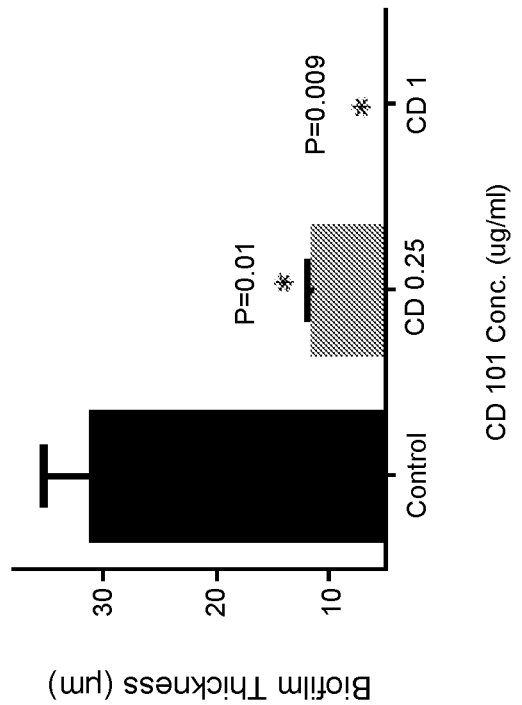

Our metabolic activity and CSLM results showed that CD101 prevented formation of robust biofilms at both concentrations tested (0.25 and 1 µg/ml). Assessment of metabolic activity revealed that *C. albicans* treated with CD101 formed significantly less biofilms compared to untreated *C. albicans* (FIG. 2A, P<0.05), In contrast, fluconazole did not inhibit biofilm formation at the two concentrations tested (1 and 4 µg/ml, FIG. 2B, P>0.05). CSLM images showed highly heterogeneous architecture of biofilms with cells/hyphae embedded within extracellular matrix for untreated control (FIG. 3A) while exposure to both concentrations of CD101 showed only remnants of adhered cells, and no biofilm maturation (FIGS. 3B and 3C). In contrast, fluconazole did not inhibit biofilm formation (FIGS. 3D and 3E). Additionally, exposure to CD101 significantly reduced the thickness of biofilms compared to untreated control (36 µm vs. 4 µm, P<0.05, FIG. 3F), while fluconazole had no effect on biofilm thickness (FIG. 3G).

Activity Against Mature Phase Biofilms (Treatment)

Figure 4A:
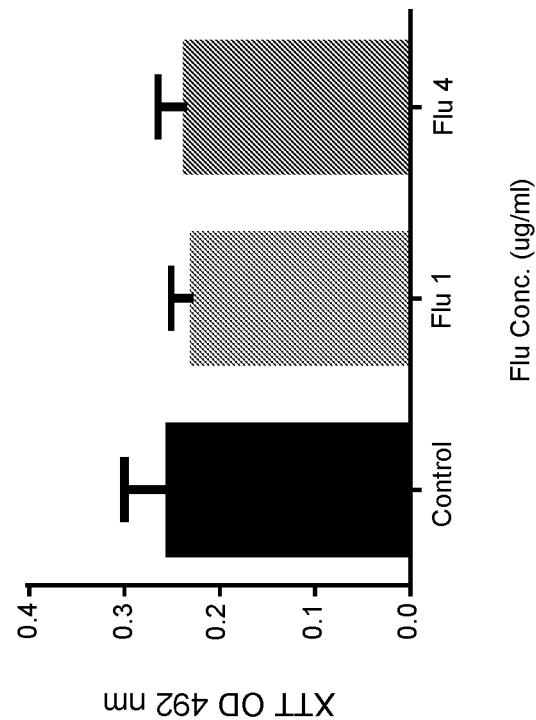
FIGS. 4A and 4B are bar graphs showing the effect of CD101 (0.25 or 1 μg/ml) (FIG. 4A) and fluconazole (1 or 4 μg/ml) (FIG. 4B) on metabolic activity of mature phase *C. albicans* biofilms compared to untreated control.
Figure 4B:
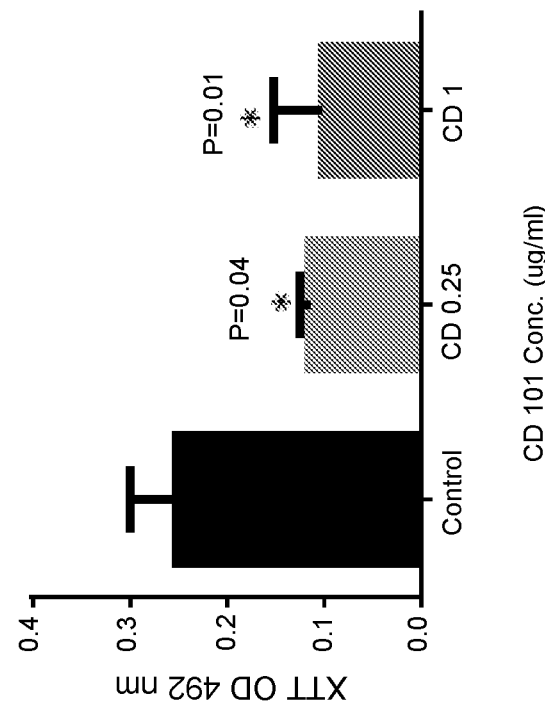
Figure 5G:
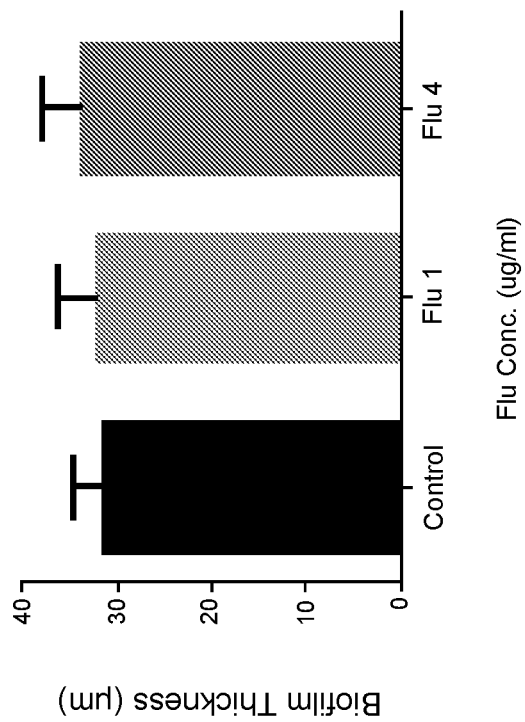
FIGS. 5F and 5G are bar graphs showing thickness of *C. albicans* biofilms exposed to: CD101 (FIG. 5F) and fluconazole (FIG. 5G).
Figure 5F:
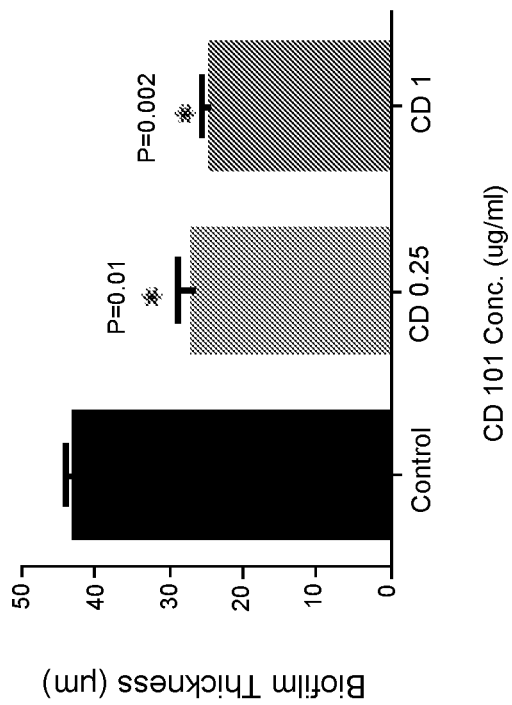

Metabolic activity and CSLM results showed that CD101 was active against mature biofilms at both tested concentrations (0.25 and 1 µg/ml). Mature *C. albicans* biofilms exposed to CD101 exhibited significantly less metabolic activity compared to those formed by untreated biofilms (FIG. 4A, P<0.05). In contrast, neither concentrations of fluconazole (1 and 4 µg/ml) affected these biofilms (FIG. 4B, P>0.05 compared to untreated controls). CSLM analyses showed highly heterogeneous architecture of biofilms for untreated control (FIG. 5A), while biofilm treated with CD101 were eradicated and showed bulged, deformed/broken cells (FIGS. 5B and 5C). In contrast, fluconazole did not affect *Candida* biofilms at both concentrations used (FIGS. 5D and 5E). Additionally, CD101 significantly reduced thickness of biofilms compared to untreated control (43 µm vs. 24 µm, P<0.05, FIG. 5F) while fluconazole had no effect (FIG. 5G).

Time Lapse

Figure 6B:
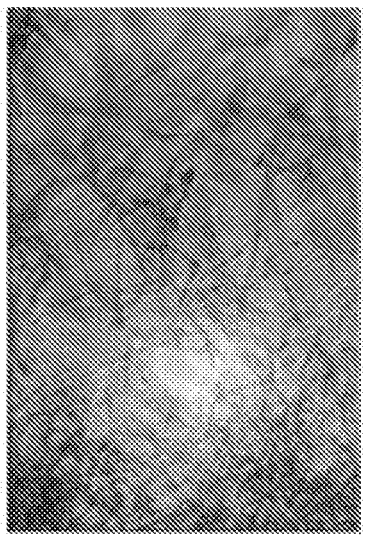
FIGS. 6A-6F are images showing the temporal effect of CD101 (0.25 μg/ml) on formation of *C. albicans* biofilms. Images were captured immediately from 0 h and followed up to 16 h for biofilms treated with: no drug (FIGS. 6A and 6B), CD101 at low magnification, ×20 (FIGS. 6C and 6D), and CD101 at high magnification, ×63 (FIGS. 6E and 6F). Arrows show bulging, deformed, and broken cells.
Figure 6A:
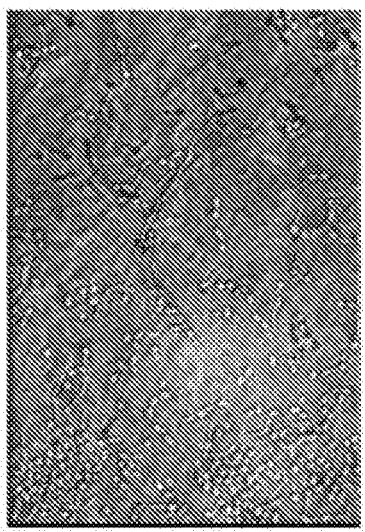
Figure 6C:
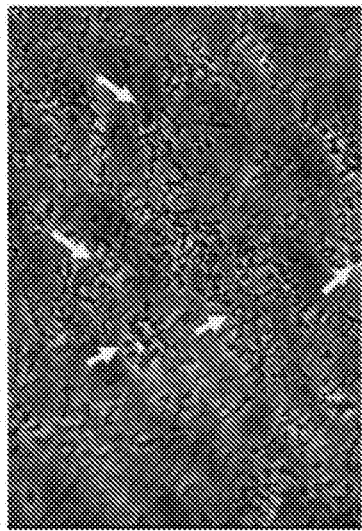
Figure 6D:
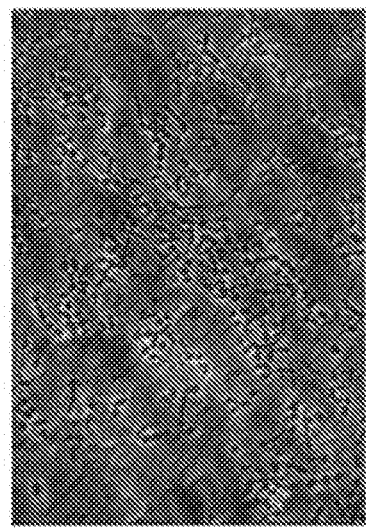
Figure 6E:
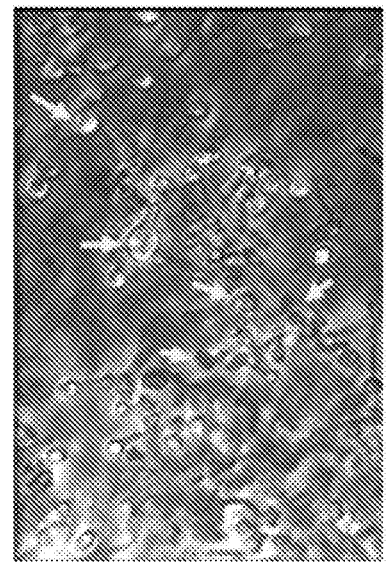
Figure 6F:
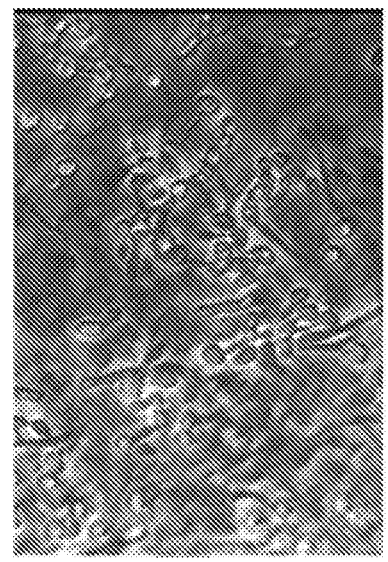

Time lapse movies showed that untreated biofilms formed highly heterogeneous architecture of biofilms with cells/hyphae embedded within extracellular matrix (screen frames in FIGS. 6A and 6B). In contrast, biofilms exposed to 0.25 µg/ml CD101 showed only adhered cells with stunted growth, which failed to grow into mature biofilms (FIGS. 6C-6F). Under high magnification, bulging, deformed, and broken cells were clearly visible (arrows, FIGS. 6D and 6F). The effect of CD101 (0.25 µg/ml) was also studied on 3 h formed biofilms and images were captured immediately after adding the drug and followed up to 16 h. Screen frames in FIG. 7A showed 3 h biofilm hyphal growth which after adding drug remained stunted and failed to grow into mature biofilms (FIG. 7B). Bulged, deformed, broken cells/hypha were clearly visible after 16 h (arrows, FIG. 7B).

Conclusion

Our results demonstrate that CD101 possesses anti-biofilm activity against both adhesion phase and mature phase biofilms formed by *C. albicans*. This antifungal agent may have utility in both prevention and treatment of fungal biofilm infections.

OTHER EMBODIMENTS

All publications, patents, and patent applications mentioned in this specification are herein incorporated by reference to the same extent as if each independent publication or patent application was specifically and individually indicated to be incorporated by reference.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure that come within known or customary practice within the art to which the disclosure pertains and may be applied to the essential features hereinbefore set forth, and follows in the scope of the claims.

Other embodiments are within the claims.

What is claimed is:

1. A pharmaceutical composition for intravenous injection comprising an aqueous solution comprising at least 85% (w/w) water, from 0.8 mg/mL to 1.6 mg/mL CD101 acetate, from 0.12% to 0.6% (w/w) of a saccharide, and an intravenous solubility promoter, and wherein the weight to weight (w/w) ratio of the intravenous solubility promoter to the CD101 in the pharmaceutical composition is at least 2.

2. The pharmaceutical composition of claim 1, wherein the w/w ratio of the intravenous solubility promoter to the CD101 in the pharmaceutical composition is between 2 and 8.

3. The pharmaceutical composition of claim 1, wherein the intravenous solubility promoter is selected from the group consisting of polysorbate 20, polysorbate 40, polysorbate 60, polysorbate 80, β-cyclodextrin, polyoxyl 35 castor oil, polyoxyl 40 hydrogenated castor oil, polyoxyl 60 hydrogenated castor oil, D-a-tocopheryl polyethylene glycol 1000 succinate, sorbitan monooleate, polyoxyl 8 stearate, polyoxyl 40 stearate, PEG 400 caprylic/capric glycerides, PEG 300 oleic glycerides, phosphatidylcholine, alkylglucoside, sucrose monolaurate, sucrose monooleate, and polyoxyethylene-polyoxypropylene block copolymer.

4. The pharmaceutical composition of claim 3, wherein the intravenous solubility promoter is polysorbate 80.

5. The pharmaceutical composition of claim 1, further comprising a buffer.

6. A pharmaceutical composition comprising an effective amount of CD101 acetate, from 2% to 10% (w/w) of a saccharide, and an intravenous solubility promoter in a lyophilized composition, wherein the weight to weight (w/w) ratio of the intravenous solubility promoter to the CD101 in the lyophilized composition is between 2 and 8.

7. A method of treating or preventing a fungal infection in a subject, comprising intravenously administering the pharmaceutical composition of claim 1 to the subject.

8. A method of treating or preventing a fungal infection in a subject, comprising:
(i) reconstituting the pharmaceutical composition of claim 6 to form an aqueous solution; and
(ii) intravenously administering the aqueous solution to the subject,
wherein the concentration of the CD101 acetate in the aqueous solution is from 0.8 mg/mL to 1.6 mg/mL.

9. The method of claim 7, comprising intravenously administering to the subject by infusion.

10. The method of claim 7, comprising intravenously administering to the subject by infusion at a constant infusion rate of between 2 ml/minute and 9 ml/minute.

11. The method of claim 7, comprising intravenously administering to the subject by infusion over 30 to 120 minutes.

12. The method of claim 7, comprising intravenously administering one dose every 5 to 15 days.

13. The method of claim 7, wherein the fungal infection to be treated or prevented is selected from candidemia, invasive candidiasis, *Tinea capitis, Tinea corporis, Tinea pedis*, onychomycosis, perionychomycosis, *Pityriasis versicolor*, oral thrush, vaginal candidiasis, respiratory tract candidiasis, biliary candidiasis, eosophageal candidiasis, urinary tract candidiasis, systemic candidiasis, mucocutaneous candidiasis, aspergillosis, mucormycosis, paracoccidioidomycosis, North American blastomycosis, histoplasmosis, coccidioidomycosis, sporotrichosis, fungal sinusitis, or chronic sinusitis.

* * * * *